(12) United States Patent
Chishti et al.

(10) Patent No.: US 7,435,083 B2
(45) Date of Patent: *Oct. 14, 2008

(54) TOOTH PATH TREATMENT PLAN

(75) Inventors: Muhammad Chishti, Sunnyvale, CA (US); Huafeng Wen, Redwood Shores, CA (US); Woncheol Choi, San Jose, CA (US)

(73) Assignee: Align Technology, Inc., Santa Clara, CA (US)

( * ) Notice: Subject to any disclaimer, the term of this patent is extended or adjusted under 35 U.S.C. 154(b) by 237 days.

This patent is subject to a terminal disclaimer.

(21) Appl. No.: 11/096,627

(22) Filed: Mar. 31, 2005
(Under 37 CFR 1.47)

(65) Prior Publication Data

US 2007/0003907 A1 Jan. 4, 2007

Related U.S. Application Data

(63) Continuation of application No. 10/751,847, filed on Jan. 5, 2004, now abandoned, which is a continuation of application No. 09/943,097, filed on Aug. 29, 2001, now Pat. No. 6,729,876, which is a continuation-in-part of application No. 09/313,289, filed on May 13, 1999, now Pat. No. 6,318,994, and a continuation-in-part of application No. 10/404,178, filed on Mar. 31, 2003, and a continuation of application No. 09/843,246, filed on Apr. 25, 2001, now Pat. No. 6,602,070, which is a continuation-in-part of application No. 09/313,289, filed on May 13, 1999, now Pat. No. 6,318,994.

(60) Provisional application No. 60/199,610, filed on Apr. 25, 2000.

(51) Int. Cl.
*A61C 3/00* (2006.01)
(52) U.S. Cl. .................................... 433/24; 433/213
(58) Field of Classification Search ............... 433/24, 433/213
See application file for complete search history.

(56) References Cited

U.S. PATENT DOCUMENTS

| 2,467,432 | A | 4/1949 | Kesling |
| 3,660,900 | A | 5/1972 | Andrews |
| 3,860,803 | A | 1/1975 | Levine |
| 3,916,526 | A | 11/1975 | Schudy |
| 3,950,851 | A | 4/1976 | Bergersen |

(Continued)

FOREIGN PATENT DOCUMENTS

EP 0091876 A1 10/1983

(Continued)

OTHER PUBLICATIONS

Alexander et al., "The DigiGraph Work Station Part 2, Clinical Management," *JCO* (Jul. 1990), pp. 402-407.

(Continued)

*Primary Examiner*—John J Wilson
(74) *Attorney, Agent, or Firm*—Townsend and Townsend and Crew

(57) ABSTRACT

Systems and methods are disclosed to prepare a malocclusion treatment plan by selecting a tooth treatment pattern from a library of predetermined tooth treatment patterns; and generating the malocclusion treatment plan implementing the selected tooth treatment pattern.

19 Claims, 20 Drawing Sheets

U.S. PATENT DOCUMENTS

| | | |
|---|---|---|
| 4,014,096 A | 3/1977 | Dellinger |
| 4,195,046 A | 3/1980 | Kesling |
| 4,324,546 A | 4/1982 | Heitlinger et al. |
| 4,348,178 A | 9/1982 | Kurz |
| 4,478,580 A | 10/1984 | Barrut |
| 4,504,225 A | 3/1985 | Yoshii |
| 4,505,673 A | 3/1985 | Yoshii |
| 4,575,805 A | 3/1986 | Moermann et al. |
| 4,611,288 A | 9/1986 | Duret et al. |
| 4,656,860 A | 4/1987 | Orthuber et al. |
| 4,663,720 A | 5/1987 | Duret et al. |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,837,732 A | 6/1989 | Brandestini et al. |
| 4,850,864 A | 7/1989 | Diamond |
| 4,856,991 A | 8/1989 | Breads et al. |
| 4,936,862 A | 6/1990 | Walker et al. |
| 4,937,928 A | 7/1990 | van der Zel |
| 4,964,770 A | 10/1990 | Steinbichler et al. |
| 4,975,052 A | 12/1990 | Spencer et al. |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,128,870 A | 7/1992 | Erdman et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,496 A | 8/1995 | Andersson et al. |
| 5,447,432 A | 9/1995 | Andersson et al. |
| 5,452,219 A | 9/1995 | Dehoff et al. |
| 5,453,009 A | 9/1995 | Feldman |
| 5,454,717 A | 10/1995 | Andreiko et al. |
| 5,456,600 A | 10/1995 | Andreiko et al. |
| 5,474,448 A | 12/1995 | Andreiko et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,587,912 A | 12/1996 | Andersson et al. |
| 5,605,459 A | 2/1997 | Kuroda et al. |
| 5,607,305 A | 3/1997 | Andersson et al. |
| 5,645,421 A | 7/1997 | Slootsky |
| 5,655,653 A | 8/1997 | Chester |
| 5,683,243 A | 11/1997 | Andreiko et al. |
| 5,733,126 A | 3/1998 | Andersson et al. |
| 5,740,267 A | 4/1998 | Echerer et al. |
| 5,975,893 A | 11/1999 | Chishti et al. |
| 6,152,731 A | 11/2000 | Jordan et al. |
| 6,217,334 B1 | 4/2001 | Hultgren |
| 6,318,994 B1 | 11/2001 | Chishti et al. |
| 6,729,876 B2 | 5/2004 | Chishti et al. |

FOREIGN PATENT DOCUMENTS

| | | |
|---|---|---|
| EP | 0299490 A2 | 1/1989 |
| EP | 0376873 A2 | 7/1990 |
| EP | 0490848 A2 | 6/1992 |
| EP | 0774933 B1 | 5/1997 |
| EP | 0541500 A1 | 6/1998 |
| EP | 0731673 B1 | 9/1998 |
| FR | 2369828 A1 | 6/1978 |
| FR | 2652256 A1 | 3/1991 |
| WO | WO 90/08512 A1 | 8/1990 |
| WO | WO 91/04713 A1 | 4/1991 |
| WO | WO 94/10935 A1 | 5/1994 |
| WO | WO 98/44865 A1 | 10/1998 |
| WO | WO 98/58596 A1 | 12/1998 |

OTHER PUBLICATIONS

Altschuler et al, "Measuring Surfaces Space-Coded by a Laser-Projected Dot Matrix," *SPIE Imaging Applications for Automated Industrial Inspection and Assembly*, vol. 182 (1979), p. 187-191.

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, *Journal of Dental Research*, vol. 58, Jan. 1979, Special Issue A, p. 221.

Altschuler et al., "Laser Electro-Optic System for Rapid Three-Dimensional (3D) Topographic Mapping of Surfaces," *Optical Engineering*, vol. 20(6) (1981), pp. 953-961.

Altschuler, "3D Mapping of Maxillo-Facial Prosthesis," AADR Abstract #607, 1980, 1 page total.

American Association for Dental Research, Summary of Activities, Mar. 20-23, 1980, Los Angeles, CA, p. 195.

Andersson et al., "Clinical Results with Titanium Crowns Fabricated with Machine Duplication and Spark Erosion," *Acta Odontological Scandinavia*, vol. 47 (1989), pp. 279-286.

Baumrind et al., "A Stereophotogrammetric System for the Detection of Prosthesis Loosening in Total Hip-Arthroplasty", NATO Symposium on Applications of Human Biostereometrics, Jul. 9-13, 1978, SPIE vol. 166, pp. 112-123.

Baumrind et al., Mapping the Skull in 3-D, Reprinted from The Journal, *California Dental Association*, vol. 48, No. 2 (1972 Fall issue) 11 pages total.

Baumrind, "A System for Craniofacial Mapping, Through the Integration of Data from Stereo X-Ray Films and Stereo Photographs," An invited paper submitted to the 1975 American Society of Photogram. Symposium on Close-Range Photogram. Systems, University of Ill., Aug. 26-30, 1975, pp. pp. 142-166.

Baumrind, "Integrated Three-Dimensional Craniofacial Mapping: Background, Principles, and Perspectives," *Seminars in Orthodontics*, vol. 7, No. 4 (Dec. 2001), pp. 223-232.

Begole et al., "A Computer System for the Analysis of Dental Casts," *The Angle Orthodontist*, vol. 51 No. 3 (Jul. 1981), pp. 253-259.

Bernard et al., "Computerized Diagnosis in Orthodontics for Epidemiological Studies: A Progress Report", Abstracts of Papers, *Journal of Dental Research*; vol. 67, Special Issue Mar. 9-13, 1988, p. 169.

Bhatia et al., "A Computer-Aided Design for Orthognathic Surgery," *British Journal of Oral and Maxillofacial Surgery*, vol. 22 (1984), pp. 237-253.

Biggerstaff et al., "Computerized Analysis of Occlusion In The Postcanine Dentition," *American Journal of Orthodontics*, vol. 61, No. 3 (Mar. 1972), pp. 245-254.

Biggerstaff, "Computerized Diagnostic Setups and Simulations," *The Angle Orthodontist*, vol. 40, No. 1 (Jan. 1970), pp. 28-36.

Biostar Operation & Training Manual, Great Lakes Orthodontics, Ltd. 199 Fire Tower Drive, Tonawanda, New York, 14150-5890.

Boyd et al., "Three Dimensional Diagnosis and Orthodontic Treatment of Complex Malocclusions with the Invisalign Appliance", *Seminars in Orthodontics*, vol. 7, No. 4 (Dec. 2001), p. 274-293.

Brandestini et al., "Computer Machined Ceramic Inlays: In Vitro Marginal Adaptation," *Journal of Dental Research*, vol. 64/Special Issue/Abstracts, IADR/AADR Abstracts 1985, p. 208.

Brook et al., An Image Analysis System for the Determination of Tooth Dimensions from Study Casts: Comparison with Manual Measurements of Mesio-distal Diameter, *J Dent Res.*, vol. 65, No. 3, Mar. 1986, pp. 428-431.

Burstone (interview), "Dr. Charles J. Burstone on The Uses of the Computer in Orthodontic Practice (Parts1 and 2)," *Journal of Clinical Orthodontics*, (Part 1) vol. 8, No. 7, Jul. 1979; (Part 2) vol. 8, No. 8 pp. 539-551, Aug. 1979.

Burstone et al., "Precision Adjustment of the Transpalatal Lingual Arch: Computer Arch Form Predetermination," *Am. Journal of Orthodontics*, vol. 79, No. 2 (Feb. 1981), pp. 115-133.

Chaconas et al., "The DigiGraph Work Station, Part 1, Basic Concepts," *JCO* (Jun. 1990), pp. 360-367.

Chafetz et al., "Subsidence of the Femoral Prosthesis, A Stereophotogrammetric Evaluation," *Clinical Orthopaedics and Related Research*, No. 201 (Dec. 1985), pp. 60-67.

Chiappone, "Constructing the Gnathologic Setup And Positioner" *J. Clin. Orthod.*, 14:121-133, 1980.

Cottingham, "Gnathologic Clear Plastic Positioner" *Am. J. Orthod.*, vol. 55, No. 1, (Jan. 1969),. pp. 23-31.

Crawford, "Computers in Dentistry: Part 1: CAD/CAM: The Computer Moves Chairside," "Part 2: F. Duret—A Man With A Vision," "Part 3: The Computer Gives New Vision- Literally," "Part 4: Bytes 'N Bites" The Computer Moves From The Front Desk To The Operatory, *Canadian Dental Journal*, vol. 54(9), , (1988), pp. 661-666.

Crawford, "CAD/CAM in the Dental Office: Does it Work?" *Canadian Dental Journal*, vol. 57, No. 2 (Feb. 1991), pp. 121-123.

Crooks, "CAD/CAM Comes to USC," *USC Dentistry*, (Spring 1990) pp. 14-17.

Cureton, "Correcting Malaligned Mandibular Incisors With Removable Retainers" *J. Clin. Orthod.*, 30:390-395, 1996.

Curry et al., "Integrated Three-Dimensional Craniofacial Mapping at the Craniofacial Research Instrumentation Laboratory/University of the Pacific," *Seminars in Orthodontics*, vol. 7, No. 4 (Dec. 2001), pp. 258-265.

Cutting et al., "Three-Dimensional Computer-Assisted Design of Craniofacial Surgical Procedures: Optimization and Interaction with Cephalometric and CT-Based Models," *Plastic and Reconstructive Surgery*, vol. 77, No. 6 (Jun. 1986), pp. 877-885.

DCS Dental AG, "The CAD/CAM 'DCS Titan System' for Production of Crowns/Bridges" *DSC Production AG*, Jan. 1992, pp. 1-7.

Defranco et al., "Three-Dimensional Large Displacement Analysis of Orthodontic Appliances," *J. Biomechanics*, vol. 9 (1976), pp. 793-801.

Dental Institute University of Zurich Switzerland, Program for International Symposium on Computer Restorations: State of the Art of the CEREC-Method, May 1991, 2 pages total.

DenTrac Corporation, Dentrac document, pp. 4-13.

Doyle, "Digital Dentistry" *Computer Graphics World* (Oct. 2000) pp. 50-52, 54.

Duret et al, "CAD-CAM in Dentistry," *Journal of the American Dental Association*, vol. 117 (Nov. 1988), pp. 715-720.

Duret et al., "CAD/CAM Imaging in Dentistry," *Current Opinion in Dentistry*, vol. 1 (1991), pp. 150-154.

Duret, "Vers une prosthese informatisee," (English translation also attached), *Tonus*, vol. 75 (Nov. 15, 1985), pp. 55-57.

Duret, "The Dental CAD/CAM, General Description of the Project," *Hennson International Product Brochure*, Jan. 1986., 18 pages total.

Economides, "The Microcomputer in the Orthodontic Office," *JCO*, (Nov. 1979), pp. 767-772.

Elsasser, "Some Observations on the History and Uses of the Kesling Positioner" *Am. J. Orthod.*, vol. 36, No. 5, (May 1950) pp. 368-374.

Faber et al., "Computerized interactive orthodontic treatment planning," *Am. J. Orthod.*, vol. 73, No. 1 (Jan. 1978), pp. 36-46.

Felton et al. "A computerized analysis of the shape and stability of mandibular arch form," *Am. Journal of Orthodontics and Dentofacial Orthopedics*, vol. 92, No. 6 (Dec. 1987), pp. 478-483.

Kesling, "The Philosophy of the Tooth Positioning Appliance" *Am. J. Orthod. Oral. Surg.*, 31(6):297-304, 1945.

Kleemann et al., "The Speed Positioner" *J. Clin. Orthod.*, 30:673-680, 1996.

Kuroda et al., "Three-dimensional dental cast analyzing system using laser scanning" *Am. J. Orthod. Dentofac. Orthop.*, 110:365-369, 1996.

Laurendeau et al., "A Computer-Vision Technique for the Acquisition and Processing of 3-D Profiles of Dental Imprints: An Application in Orthodontics," *IEEE Transactions on Medical Imaging*, vol. 10, No. 3 (Sep. 1991), pp. 453-461.

Lawrence, "The Six to Normal Occlusion," Am. J. Orthodont. Sep. 1972, 296,308.

Lawrence., "Straight Wire, The Concept and Appliance," *The Six Keys to Optimal Occlusion*, 15-24.

Leinfelder et al., "A new method for generating ceramic restorations: a CAD-CAM system," *Journal Of The American Dental Assoc.*, vol. 118, No. 6 (Jun. 1989), pp. 703-707.

Manetti et al., "Computer-aided Cefalometry and New Mechanics in Orthodontics" (Article Summary in English, article in German), *Fortschr. Kieferothop.* 44, 370-376 (Nr. 5), 1983.

McCann, Inside the ADA, *Journal Of The American Dental Assoc.*, vol. 118 (Mar. 1989) pp. 286-294.

McNamara et al., "Invisible Retainers", *J. Clinical Orthodontics*, (Aug. 1985) pp. 570-578.

McNamara et al., Chapter 19: Invisible Retainers, *Orthodontic and Orthopedic Treatment in the Mixed Dentition*, Needham Press, Jan. 1993. pp. 347-353.

Moermann et al., "Computer Machined Adhesive Porcelain Inlays: Margin Adaptation after Fatigue Stress," IADR Abstract 339, *Journal of Dental Research*, vol. 66(a) (1987), p. 763.

Mörmann et al., Marginal Adaptation von adhasiven Porzellaninlays in vitro, *Schwizerische Monatsshrift fur Zahnmedizin*, vol. 85 (1985), p. 1118-1129.

Nahoum, "the Vacuum Formed Dental Contour Appliance" *The New York State Dental Journal*, 30(9):385-390, Nov. 1964.

Nash, "Cerec CAD/CAM Inlays: Aesthetics and Durability in a Single Appointment," *Dentistry Today*, (Oct. 1990), pp. 20, 22-23, 54.

Nishiyama et al., "A New Construction Of Tooth Repositioner By LTV Vinyl Silicone Rubber" J. Nihon University School of Dentistry, 19(2):93-102, 1977.

Friede et al., Accuracy of Cephalometric Prediction in Orthognathic Surgery, Abstract of Papers, *Journal of Dental Research*, vol. 70 (1987), pp. 754-760.

Gim-Alldent Deutschland, "Das DUX System: Die Technik" 2 pages total.

Grayson, "New Methods for Three Dimensional Analysis of Craniofacial Deformity," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5-6.

Guess et al., "Computer Treatment Estimates in Orthodontics and Orthognathic Surgery," *JCO*, (Apr. 1989), pp. 262-28.

Heaven et al., "Computer-based Image Analysis of Artifical Root Surface Caries," Abstracts of Papers, *Journal of Dental Research*, vol. 70,Apr. 17-21, 1991, p. 528.

Hoffmann et al., "Role of Cephalometry for Planning of Jaw Orthopedics and Jaw Surgery Procedures," (Article Summary in English, article in German), *Informationen*, (Mar. 1991), pp. 375-396.

Huckins, "CAD-CAM Generated Mandibular Model Prototype from MRI Data," *AAOMS* 1999, p. 96.

JCO Interviews, "Craig Andreiko , DDS, MS on the Elan and Orthos Systems", JCO, (Aug. 1994), pp. 459-468.

JCO Interviews, "Dr. Homer W. Phillips on Computers in Orthodontic Practice, Part 2," JCO, (Dec. 1983), pp. 819-831.

Jerrold, "the Problem, Electronic Data Transmission and the Law," *AJO-DO*, (Apr. 1988), pp. 478-479.

Jones et al., "An Assessment of the Fit of a Parabolic Curve to Pre- and Post-Treatment Dental Arches," *British Journal of Orthodontics*, vol. 16 (1989), pp. 85-93.

Kamada et al., "Case Reports on Tooth Positioners Using LTV Vinyl Silicone Rubber" J. Nihon University School of Dentistry, 26(1):11-29, 1984.

Kamada et al., "Construction of Tooth Positioners With LTV Vinyl Silicone Rubber and Some Case Reports" J. Nihon University School of Dentistry, 24(1):1-27, 1982.

Kanazawa et al., "Three-Dimensional Measurements of the Occlusal Surfaces of Upper Molars in a Dutch Population," *J. Dent Res.*, vol. 63, No. 11 (Nov. 1984), pp. 1298-1301.

Kesling, "Coordinating the Predetermined Pattern and Tooth Positioner With Conventional Treatment" *Am. j. Orthod. Oral. Surg.*, 32:285-293, 1946.

Nippon Dental Review, "New orthodontic device-dynamic positioner (D.P.)-I Approach to the proposal of D.P. and transparent silicone rubber," 1980, 452:61-74.

Nippon Dental Review, "New orthodontic device-dynamic positioner (D.P.)-II, Practice application and construction of D.P. and transparent silicone rubber," 1980, 454:107-130.

Nippon Dental Review, "New orthodontic device-dynamic positioner (D.P.)-III, Case reports of reversed occlusion," 457:146-164.

Nippon Dental Review, "New orthodontic device-dynamic positioner (D.P.)-Case reports of reversed occlusion," 1980, 458:112-129.

Pinkham, "'Foolish' Concept Propels Technology," *Dentist*, Jan./Feb. 1989, 3 pages total.

Pinkham, "Inventor's CAD/CAM May Transform Dentistry," *Dentist*, Sep. 1990, 3 pages total.

Ponitz, "Invisible Retainers", *Am. J. Orthodontics*, vol. 59, No. 3, Mar. 1971, pp. 266-272.

Procera Research Projects, *PROCERA Research Projects* 1993—Abstract Collection, 1993, pp. 3-24.

Profit et al., "The First Stage of Comprehensive Treatment: Alignment and Leveling," Comtemporary Orthodontics, Chapter 15, 470-533.

Raintree Essix & ARS Materials, Inc., Raintree Essix, Technical Magazine Table of contents and Essic Appliances, httpz://www.essix.com/magazine/default.html Aug. 13, 1997, 7 pages.

Redmond et al., "Clinical Implications of Digital Orthodontics," Am. J. Orthodont. Dentofacial Orthopedics (2000) 117(2):240-242.

Rekow, "A Review of the Developments in Dental CAD/CAM Systems,"(contains references to Japanese efforts and content of the papers of particular interest to the clinician are indicated with a one-line summary of their content in the bibliography), Dental Clinics: *Prosthodontics and Endodontics*, pp. 25-33, 1992.

Rekow, "CAD/CAM in Dentistry: A Historical Perspective and View of the Future," *Journal*, vol. 58 No. 4, (Apr. 1992), pp. 283, 287-288.

Rekow, "Computer-Aided Design and Manufacturing in Dentistry: A Review of the State of the Art," *The Journal of Prosthetic Dentistry*, vol. 58, No. 4 (Oct. 1987), pp. 512-516.

Rekow, "Dental CAD/CAM Systems: What is the State of the Art?" *Journal of the American Dental Assoc.*, vol. 122 (1991), pp. 43-48.

Rekow, Feasibility of an Automated System for Production of "Dental Restorations," Phd Thesis, Univ. of Minnesota, Nov. 1988, 244 pages total.

Richmond et al., Research Reports, "The Development of a 3D Cast Analysis System," *British Journal of Orthodontics*, vol. 13, No. 1, (Jan. 1986) pp. 53-54.

Richmond, "Recording The Dental Cast In Three Dimensions," *Am. J. Orthod. Dentofac. Orthop.*, vol. 92, No. 3, (Sep. 1987), pp. 199-206.

Rudge, "Dental arch analysis: Arch Form, A review of the literature," *European Journal of Orthodontics*, vol. 3, No. 4 (1981), pp. 279-284.

Sakuda et al., "Integrated information-processing system in clinical orthodontics: An approach with use of a computer network system," *Am. J. Orthod. Dentofac. Orthop.* vol. 101 No. 3 (Mar. 1992), pp. 210-220.

Schellhas et al., "Three-Dimensional Computed Tomography in Maxillofacial Surgical Planning," *Arch Otolambol Head Neck Surg.* vol. 114 (Apr. 1988), pp. 438-442.

Schroeder et al., "Algorithms I," *The Visualization Toolkit*, Chapter 6-9,9, 1996.

Shilliday, "Minimizing Finishing Problems With the Mini-Positioner" *Am. J. Orthod.* 59:596-599, 1971.

Siemens, "CEREC—Computer-Reconstruction," High Tech in der Zahnmedizin, 14 page total.

Sirona Dental Systems GmbH, CEREC 3D, Manuel utilisateur, Version 2.0X (in French), 2003, 114 pages total.

Stoll et al., "Computer-aided Technologies in Dentistry" (Article Summary in English, article in German), *Dtsch Zahnärztl Z* 45, 314-322, 1990.

U.S. Department of Commerce, National Technical Information Service, "Automated Crown Replication Using Solid Photography SM," Solid Photography Inc. Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050342, filed Jun. 20, 1997, 41 pages total.

Van Der Linden et al., "Three-Dimensional Analysis of Dental Casts by Means of the Optocom," *J Dent Res*, Jul.-Aug. 1972, vol. 51, No. 4, p. 1101.

Van Der Linden, "A New Method to Determine Tooth Positions and Dental Arch Dimensions," Jul.-Aug. 1972, p. 1104.

Van Der Zel, "Ceramic-fused-to-metal Restorations with a New CAD/CAM System," *Quintessence International*, vol. 24(11) (1993), pp. 769-778.

Várady et al., Reverse Engineering Of Geometric Models—An Introduction. Computer-Aided Design, 29 (4):255-268, 1997.

Warunek et al., "Clinical Use Of Silicone Elastomer Appliances" *JCO*, MH (10):694-700, 1989.

Warunek et al., "Physical And Mechanical Properties of Elastomers In Orthodontic Positioners" *Am. J. Orthod. Dentofac. Orthop.*, 95:388-400, 1989.

Wells, "Application to the Positioner Appliance in Orthodontic Treatment" *Am. J. Orthodont.*, 58:351-366, 1970.

Williams, "Dentistry and CAD/CAM: Another French Revolution," *Journal of Dental Practice Admin.*, Jan./Mar. 1987, pp. 2-5.

Williams, "The Switzerland and Minnesota Developments in CAD/CAM," *Journal of Dental Practice Admin.*, pp. 50-55, Apr./Jun. 1987.

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5.

Yamamoto et al., "Three-Dimensional Measurement of Dental Cast Profiles and its Applications to Orthodontics," Annual Int'l Conf. of IEEE Engineering in Medicine and Biology Society, vol. 12, No. 5, pp. 2051-2053, 1990.

Yamamoto et al., "Optical Measurement of Dental Cast Profile and Application to Analysis of Three-Dimensional Tooth Movement in Orthodontics," *Frontiers in Med. and Biol. Eng'g*, vol. 1, No. 2 (1988), pp. 119-130.

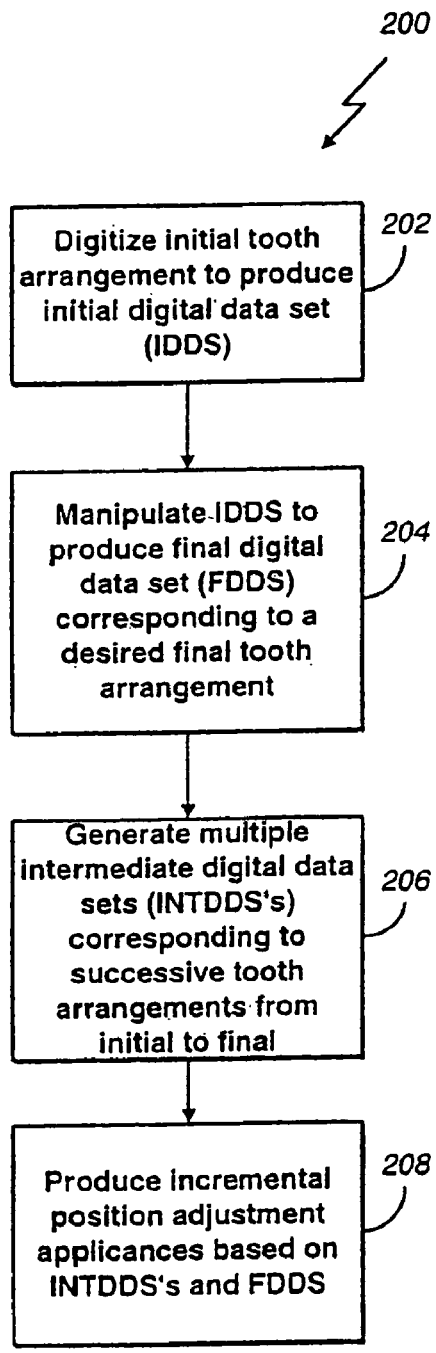
FIG._3
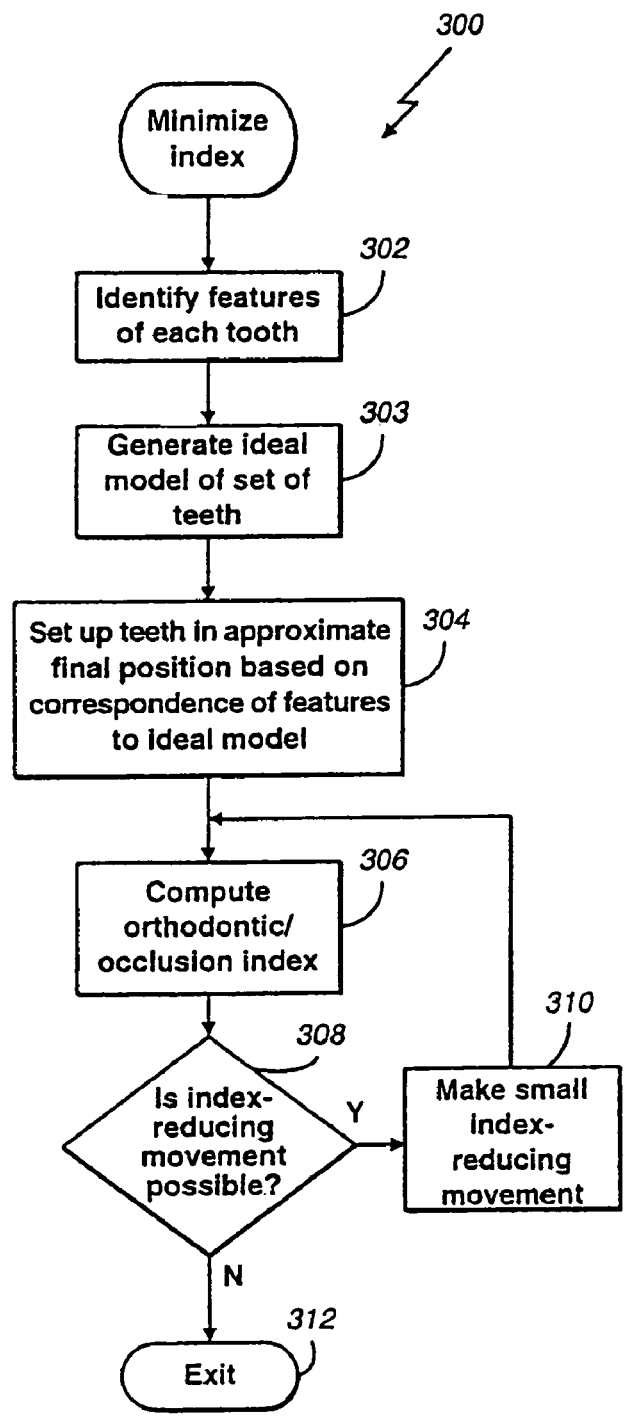
FIG._4

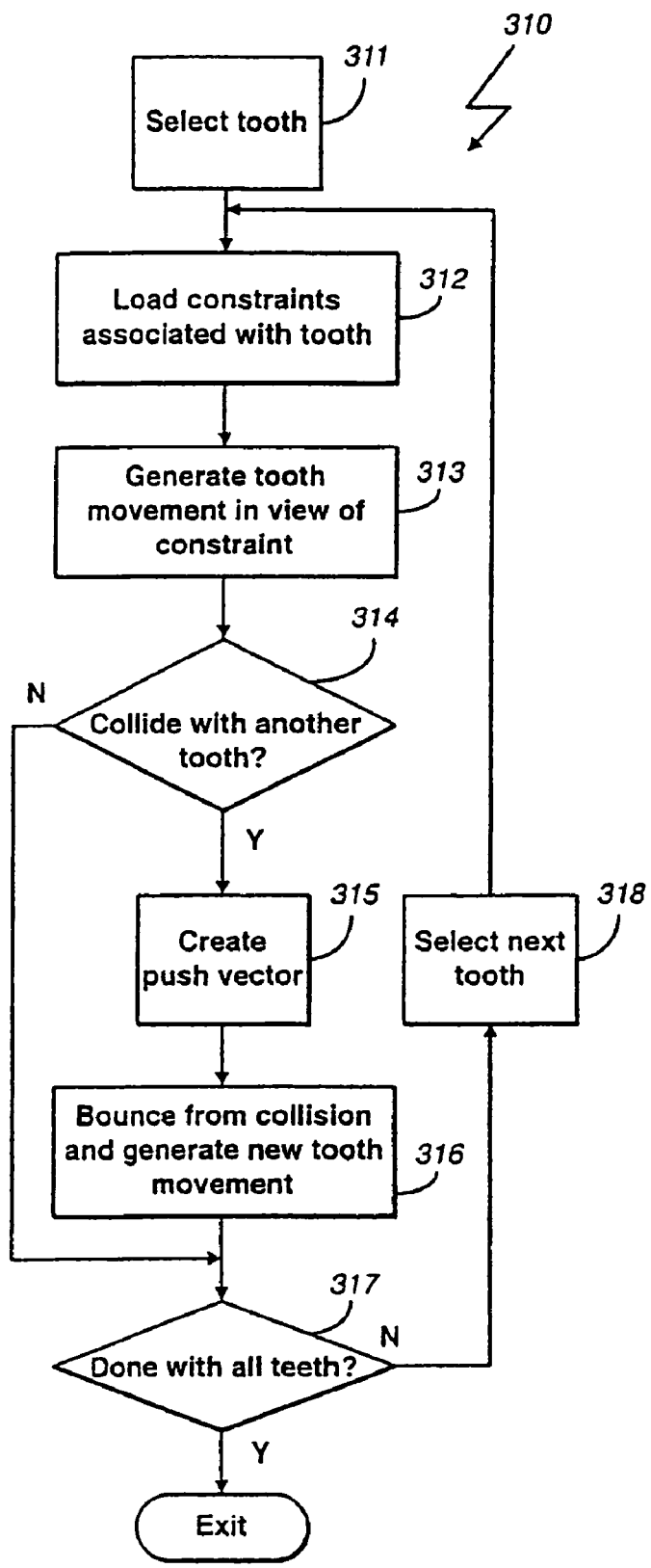
FIG._5

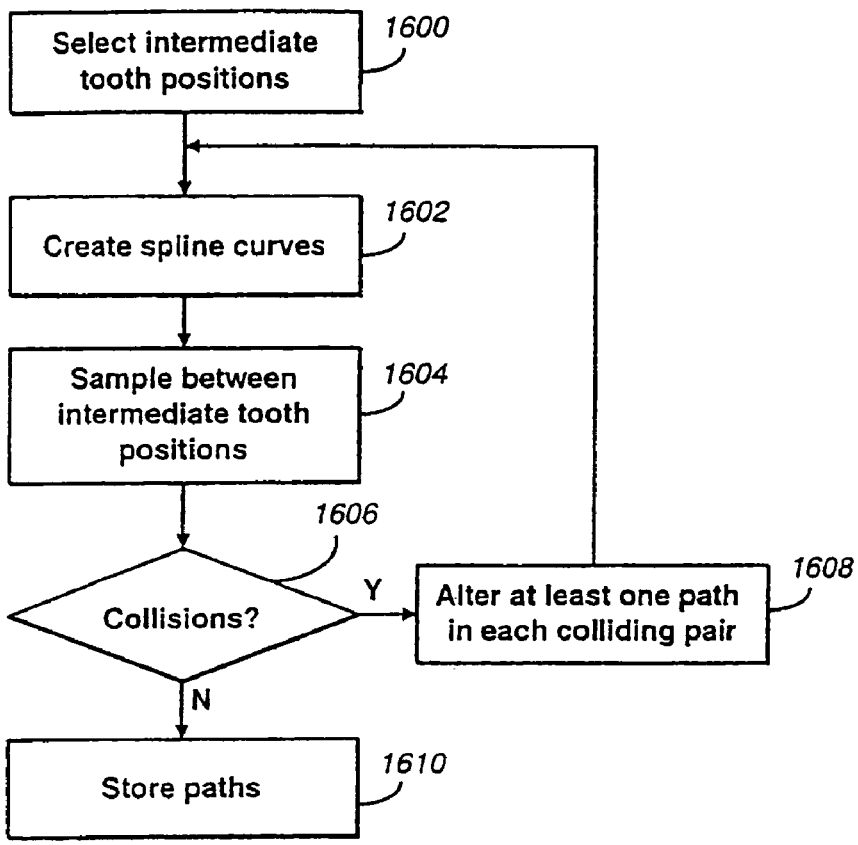
FIG._6
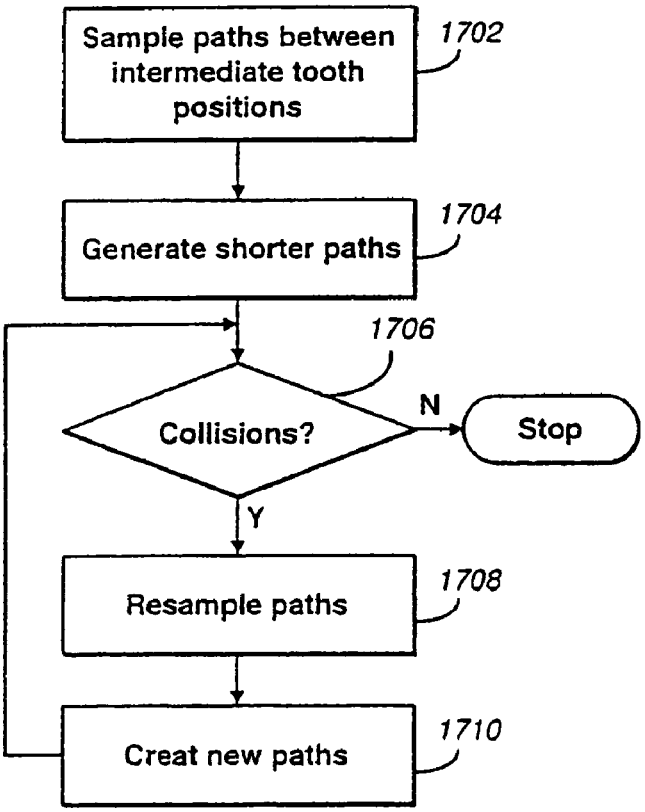
FIG._7

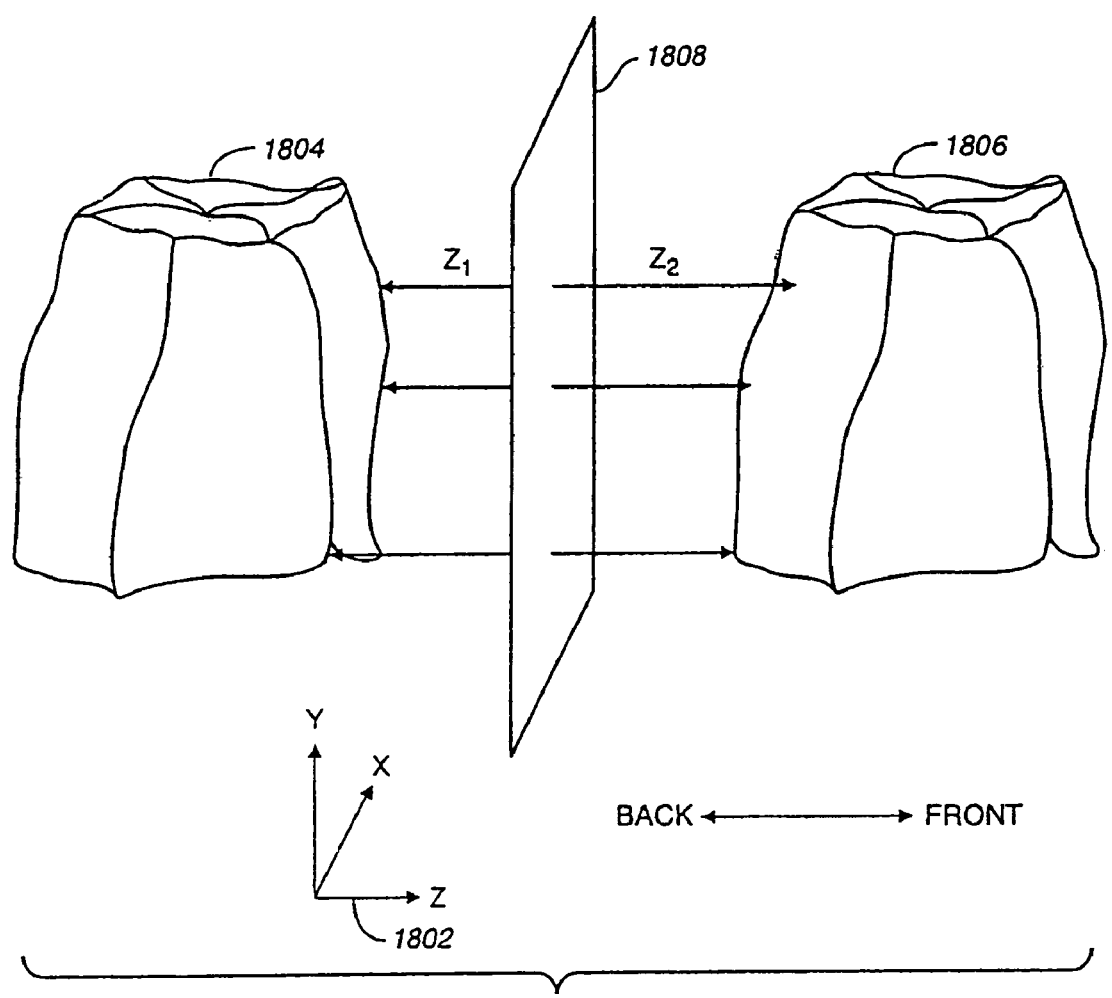
FIG._8

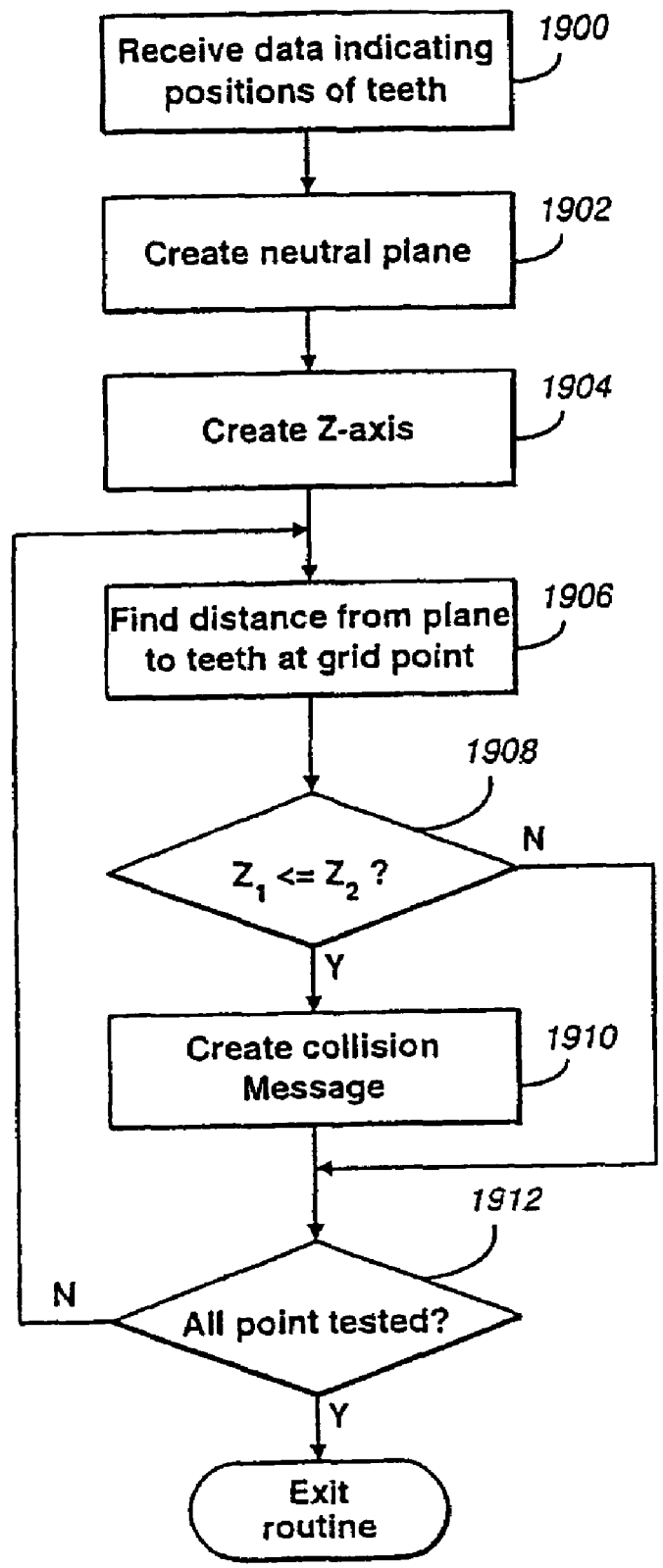
FIG._9

*Recursive Subdivision Calculation*

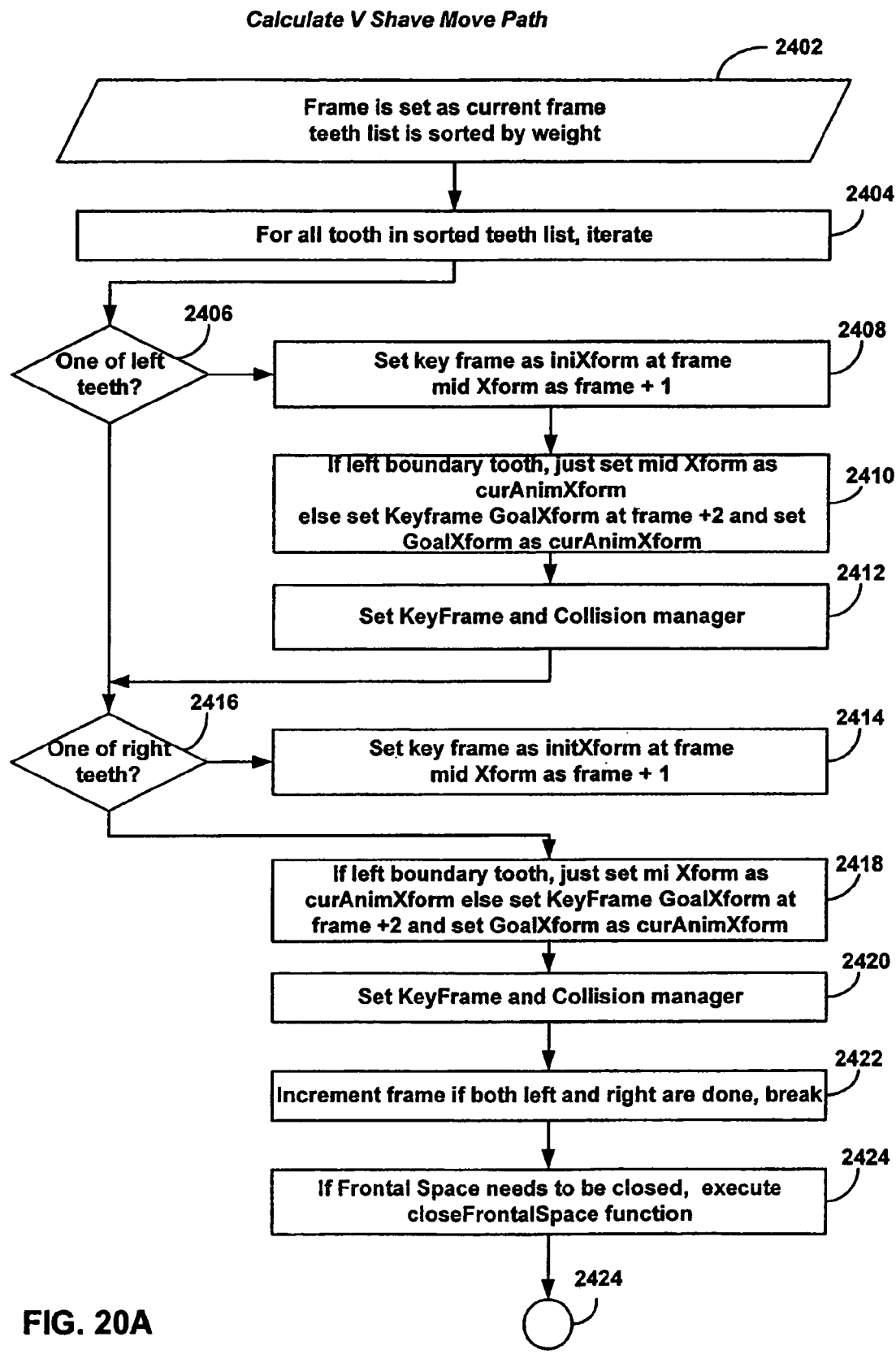

US 7,435,083 B2

TOOTH PATH TREATMENT PLAN

CROSS-REFERENCES TO RELATED APPLICATIONS

This application a continuation of U.S. patent application Ser. No. 10/751,847, filed on Jan. 5, 2004, now abandoned, which was a continuation of U.S. application No. 09/943,097, filed Aug. 29, 2001, now U.S. Pat. No. 6,729,876, which was a continuation-in-part of U.S. application No. 09/313,289, filed on May 13, 1999, now U.S. Pat. No. 6,318,994, the full disclosures of which are incorporated herein by reference.

This application is also a continuation-in-part of U.S. application Ser. No. 10/404,178, filed on Mar. 31, 2003, which was a continuation of U.S. application Ser. No. 09/843,246, filed on Apr. 25, 2001, now U.S. Pat. No. 6,602,070 B2, which was a continuation-in-part of U.S. application Ser. No. 09/313,289, filed on May 13, 1999, now U.S. Pat. No. 6,318,994, which claimed the benefit of Provisional Application No. 60/199,610, filed on Apr. 25, 2000, the full disclosures of which are incorporated herein by reference.

The present application is also related to U.S. patent application Ser. Nos. 09/169,036, now U.S. Pat. No. 6,450,807, entitled "System and Method for Repositioning Teeth" and 09/169,034, now U.S. Pat. No. 6,471,511 entitled "Defining Tooth-Moving Appliances Computationally." Both of these applications were filed Oct. 8, 1998, and the full disclosures of each are incorporated herein by reference.

BACKGROUND OF THE INVENTION

1. Field of the Invention.

The invention relates generally to the field of orthodontics and, more particularly, to computer-automated development of an orthodontic treatment plan and appliance.

2. Description of the Background Art

Repositioning teeth for aesthetic or other reasons is accomplished conventionally by wearing what are commonly referred to as "braces." Braces comprise a variety of appliances such as brackets, archwires, ligatures, and O-rings. Attaching the appliances to a patient's teeth is a tedious and time-consuming enterprise requiring many meetings with the treating orthodontist. Consequently, conventional orthodontic treatment limits an orthodontist's patient capacity and makes orthodontic treatment quite expensive. As such, the use of conventional braces is a tedious and time consuming process and requires many visits to the orthodontist's office. Moreover, from the patient's perspective, the use of braces is unsightly, uncomfortable, presents a risk of infection, and makes brushing, flossing, and other dental hygiene procedures difficult.

Tooth positioners for finishing orthodontic treatment are described by Kesling in the *Am. J. Orthod. Oral. Surg.* 31:297-304 (1945) and 32:285-293 (1946). The use of silicone positioners for the comprehensive orthodontic realignment of a patient's teeth is described in Warunek et al. (1989) *J. Clin. Orthod.* 23:694-700. Clear plastic retainers for finishing and maintaining tooth positions are commercially available from Raintree Essix, Inc., New Orleans, La. 70125, and Tru-Tain Plastics, Rochester, Minn. 55902. The manufacture of orthodontic positioners is described in U.S. Pat. Nos. 5,186,623; 5,059,118; 5,055,039; 5,035,613; 4,856,991; 4,798,534; and 4,755,139.

Other publications describing the fabrication and use of dental positioners include Kleemann and Janssen (1996) *J. Clin. Orthodon.* 30:673-680; Cureton (1996) *J. Clin. Orthodon.* 30:390-395; Chiappone (1980) *J. Clin. Orthodon.* 14:121-133; Shilliday (1971) *Am. J. Orthodontics* 59:596-599; Wells (1970) *Am. J. Orthodontics* 58:351-366; and Cottingham (1969) *Am. J. Orthodontics* 55:23-31.

Kuroda et al. (1996) *Am. J. Orthodontics* 110:365-369 describes a method for laser scanning a plaster dental cast to produce a digital image of the cast. See also U.S. Pat. No. 5,605,459.

U.S. Pat. Nos. 5,533,895; 5,474,448; 5,454,717; 5,447,432; 5,431,562; 5,395,238; 5,368,478; and 5,139,419, assigned to Ormco Corporation, describe methods for manipulating digital images of teeth for designing orthodontic appliances.

U.S. Pat. No. 5,011,405 describes a method for digitally imaging a tooth and determining optimum bracket positioning for orthodontic treatment. Laser scanning of a molded tooth to produce a three-dimensional model is described in U.S. Pat. No. 5,338,198. U.S. Pat. No. 5,452,219 describes a method for laser scanning a tooth model and milling a tooth mold. Digital computer manipulation of tooth contours is described in U.S. Pat. Nos. 5,607,305 and 5,587,912. Computerized digital imaging of the jaw is described in U.S. Pat. Nos. 5,342,202 and 5,340,309. Other patents of interest include U.S. Pat. Nos. 5,549,476; 5,382,164; 5,273,429; 4,936,862; 3,860,803; 3,660,900; 5,645,421; 5,055,039; 4,798,534; 4,856,991; 5,035,613; 5,059,118; 5,186,623; and 4,755,139.

BRIEF SUMMARY OF THE INVENTION

In one aspect, a computer-implemented method to prepare a malocclusion treatment plan includes selecting a tooth treatment pattern from a library of predetermined tooth treatment patterns; and generating the malocclusion treatment plan implementing the selected tooth treatment pattern.

Implementations of the above aspect may include one or more of the following. The generating the malocclusion treatment plan includes determining one or more tooth paths based on the selected tooth treatment pattern. The treatment pattern can be selected from one or more clinical treatment prescriptions. The clinical treatment prescription includes at least one of the following: space closure, reproximation, dental expansion, flaring, distalization, and lower incisor extraction. Determining a tooth path includes finding a collision free shortest path between an initial position and a final position for one or more teeth. Generating the malocclusion treatment plan includes specifying a series of treatment stages for one or more teeth. The method can include dividing a path for one or more teeth into the series of stages while keeping the movement of teeth in each stage below a predetermined range. The method can include generating an appliance for each treatment stage. The appliance can be either a removable appliance or a fixed appliance. The method can include generating a three-dimensional model for the teeth for each treatment stage. The method also can include generating dental diagnostic information from the three-dimensional model. Interproximal reduction, tooth size discrepancy information, and Bolton information, among others can be generated from the 3D model. The library of treatment patterns includes at least one or more of the following: all equal movement pattern, A-shaped movement pattern, V-shaped movement pattern, M-shaped movement pattern, W-shaped movement pattern, symmetric staircase pattern, asymmetric staircase pattern, and equal equal movement pattern. For the all equal movement pattern, the method includes subdividing paths while satisfying one or more constraints. The constraint can be minimizing tooth oscillation and tooth movement distance. For the equal equal pattern, the method includes dividing the teeth into a prestage movement group and a post stage movement group; and applying the all equal movement to the prestage movement group and subsequently applying the all equal movement to the prestage movement group. For the A-shaped movement pattern, the method includes sequentially moving each tooth from an incisor tooth toward a molar tooth. For the V-shaped movement pattern, the method includes sequentially moving each tooth from a molar tooth toward an incisor tooth.

In another aspect, a computer-implemented method prepares a malocclusion treatment plan by: selecting one tooth treatment pattern from a library of predetermined tooth treatment patterns; generating the malocclusion treatment plan in accordance with the selected treatment pattern; and producing a plurality of data sets representing a series of successive tooth arrangements progressing from a first tooth arrangement to a second tooth arrangement. Implementations of this aspect may include generating an appliance for each tooth arrangement.

In another aspect, a computer-readable medium executable by a computer to prepare a malocclusion treatment plan includes code to select one tooth treatment pattern from a library of predetermined tooth treatment patterns; and code to generate the malocclusion treatment plan in accordance with the selected treatment pattern.

Implementation of this aspect may include one or more of the following. The medium can include code to fabricate an appliance for each tooth arrangement. The code to fabricate appliances can include code to control a fabrication machine to produce successive positive models of the tooth arrangements; and code to produce the appliance as a negative of the tooth model. The code to control a fabrication machine includes code to provide a volume of non-hardened polymeric resin; and code to scan a laser to selectively harden a resin to produce the positive model. The medium can include code to control a fabrication machine to produce successive appliances for the tooth arrangements.

In yet another aspect, a computer-implemented method to automatically stage a series of tooth movements, by selecting one teeth treatment pattern from a plurality of predetermined teeth treatment patterns; generating a treatment plan for the teeth in accordance with the selected move pattern by: generating a treatment plan with a tooth path for each tooth; and determining a series of treatment stages for the teeth; and controlling a fabrication machine to produce successive appliances for the tooth arrangements. Implementations of this aspect may include generating an appliance as a negative or a positive of a dental model.

In another aspect, an appliance to correct malocclusion, the appliance formed using computer readable code controlling a fabrication machine, the code comprising instructions to: select one teeth treatment pattern from a plurality of predetermined teeth treatment patterns; generate a treatment plan for the teeth in accordance with the selected move pattern by: generate a treatment plan with a tooth path for each tooth; and determine a series of treatment stages for the teeth; and control the fabrication machine to produce successive appliances for the tooth arrangements.

In another aspect, a computer system to prepare a malocclusion treatment plan includes a processor; a display coupled to the processor; and a data storage device coupled to the processor and containing code to select a tooth treatment pattern from a library of predetermined tooth treatment patterns; and code to generate the malocclusion treatment plan implementing the selected tooth treatment pattern.

In yet another aspect, a computer system to prepare a malocclusion treatment plan includes means for selecting a tooth treatment pattern from a library of predetermined tooth treatment patterns; and means for generating the malocclusion treatment plan implementing the selected tooth treatment pattern.

Yet other implementations of the above aspects can include one or more of the following. The constraint relates to teeth crowding, teeth spacing, teeth extraction, teeth stripping, teeth rotation, and teeth movement. The teeth can be rotated approximately five and ten degrees (per stage) and can be incrementally moved in one or more stages (per stage), each stage moving each tooth approximately 0.2 mm to approximately 0.4 mm. The constraints can be stored in an array with one dimension of the array identifying each stage in the teeth movement. The treatment paths can include determining the minimum amount of transformation required to move each tooth from the initial position to the final position and creating each treatment path to require only the minimum amount of movement. Additionally, intermediate positions can be generated for at least one tooth between which the tooth undergoes translational movements of equal sizes. Further, intermediate positions can be generated for at least one tooth between which the tooth undergoes translational movements of unequal sizes. A set of rules can be applied to detect any collisions that will occur as the patient's teeth move along the treatment paths. Collisions can be detected by calculating distances between a first tooth and a second tooth by establishing a neutral projection plane between the first tooth and the second tooth, establishing a z-axis that is normal to the plane and that has a positive direction and a negative direction from each of a set of base points on the projection plane, computing a pair of signed distances comprising a first signed distance to the first tooth and a second signed distance to the second tooth, the signed distances being measured on a line through the base points and parallel to the z-axis, and determining that a collision occurs if any of the pair of signed distances indicates a collision. Where the positive direction for the first distance is opposite the positive direction for the second distance, a collision is detected if the sum of any pair of signed distances is less than or equal to zero. Information indicating whether the patient's teeth are following the treatment paths can be used to revise the treatment paths. More than one candidate treatment path for each tooth can be generated and graphically displayed for each candidate treatment path to a human user for selection. A set of rules can be applied to detect any collisions that will occur as the patient's teeth move along the treatment paths. Collisions can be detected by calculating distances between a first tooth and a second tooth by: establishing a neutral projection plane between the first tooth and the second tooth, establishing a z-axis that is normal to the plane and that has a positive direction and a negative direction from each of a set of base points on the projection plane, computing a pair of signed distances comprising a first signed distance to the first tooth and a second signed distance to the second tooth, the signed distances being measured on a line through the base points and parallel to the z-axis, and determining that a collision occurs if any of the pair of signed distances indicates a collision. A collision can also be detected if the sum of any pair of signed distances is less than or equal to zero. A set of rules can be applied to detect any improper bite occlusions that will occur as the patient's teeth move along the treatment paths. A value for a malocclusion index can be computed and the value displayed to a human user. The treatment paths can be generated by receiving data indicating restraints on movement of the patient's teeth and applying the data to generate the treatment paths. A three-dimensional (3D) graphical representation of the teeth at the positions corresponding to a selected data set can be rendered. The graphical representation of the teeth to provide a visual display of the movement of the teeth along the treatment paths can be generated. A graphical interface, with components representing the control buttons on a videocassette recorder, which a human user can manipulate to control the animation, can be generated. A portion of the data in the selected data set may be used to render the graphical representation of the teeth. A level-of-detail compression can be applied to the data set to render the graphical representation of the teeth. A human user can modify the graphical representation of the teeth and the selected data set can be modified in response to the user's request. A human user can select a tooth in the graphical representation and, in response, information about the tooth can be displayed. The information can relate to the motion that the tooth will experience while moving along the treatment path. The information can also indicate a linear distance between the tooth and another tooth selected in the graphical representation. The teeth can be rendered at a selected one of multiple viewing orthodontic-specific viewing angles. A user interface through which a human user can provide text-based comments after viewing the graphical representation of the patient's teeth can be provided. The graphical representation data can be downloaded to a remote computer at which a human view wishes to view the graphical representation. An input signal from a 3D gyroscopic input device controlled by a human user can be applied to alter the orientation of the teeth in the graphical representation.

Advantages of the system may include one or more of the following. The system facilitates automated staging after final setup. The system eliminates manual staging, saves time and is convenient to use. An easy to use graphical user interface supports the entry of treatment planning requirements such as particular staging pattern(s), anchorage requirement(s) (low, mid, high), and the minimum allowable tooth movements.

BRIEF DESCRIPTION OF THE DRAWINGS

FIG. 3 is a block diagram illustrating a process for producing incremental position adjustment appliances.

FIG. 4 is a flow chart illustrating a process for optimizing a final placement of the patient's teeth.

FIG. 5 is a flow chart illustrating the positioning of teeth at various steps of an orthodontic treatment plan.

FIG. 6 is a flow chart of a process for determining a tooth's path among intermediate positions during an orthodontic treatment plan.

FIG. 7 is a flow chart of a process for optimizing the path of a tooth from an initial position to a final position during an orthodontic treatment plan.

FIG. 8 is a diagram illustrating a buffering technique for use in a collision detection algorithm.

FIG. 9 is a flow chart for a collision detection technique.

FIGS. 20A-20B show an exemplary process to determine a V-shape path.

DETAILED DESCRIPTION OF THE INVENTION

Figure 1:
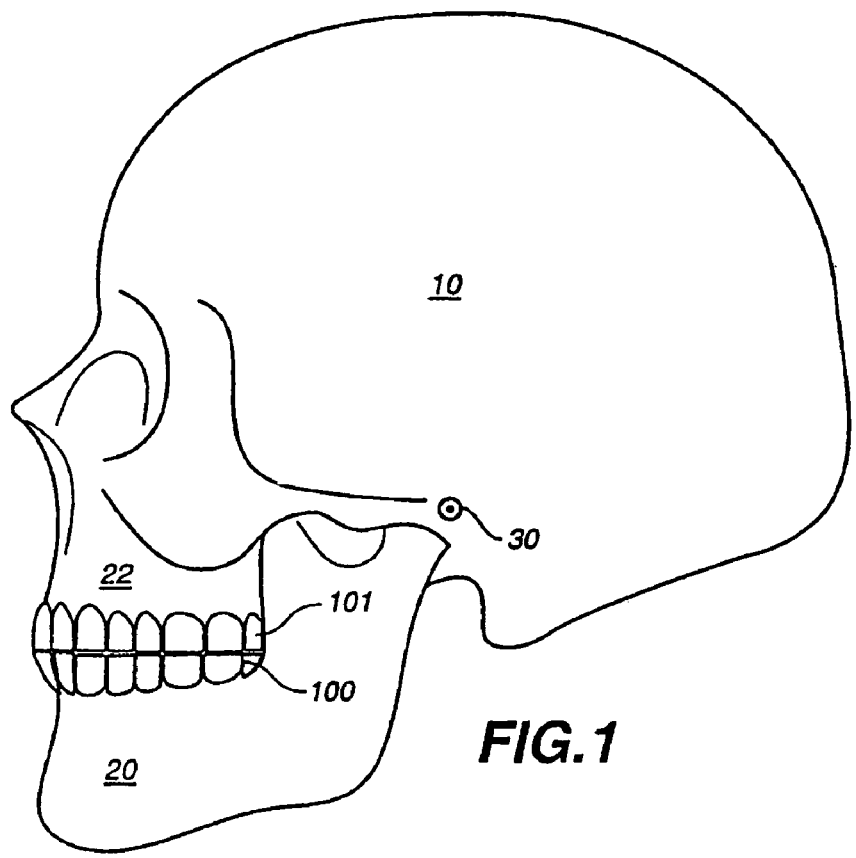
FIG. 1 is an elevational diagram showing the anatomical relationship of the jaws of a patient.

FIG. 1 shows a skull 10 with an upper jaw bone 22 and a lower jaw bone 20. The lower jaw bone 20 hinges at a joint 30 to the skull 10. The joint 30 is called a temporomandibular joint (TMJ). The upper jaw bone 22 is associated with an upper jaw 101, while the lower jaw bone 20 is associated with a lower jaw 100.

A computer model of the jaws 100 and 101 is generated, and a computer simulation models interactions among the teeth on the jaws 100 and 101. The computer simulation allows the system to focus on motions involving contacts between teeth mounted on the jaws. The computer simulation allows the system to render realistic jaw movements which are physically correct when the jaws 100 and 101 contact each other. The model of the jaw places the individual teeth in a treated position. Further, the model can be used to simulate jaw movements including protrusive motions, lateral motions, and "tooth guided" motions where the path of the lower jaw 100 is guided by teeth contacts rather than by anatomical limits of the jaws 100 and 101. Motions are applied to one jaw, but may also be applied to both jaws. Based on the occlusion determination, the final position of the teeth can be ascertained.

Figure 2A:
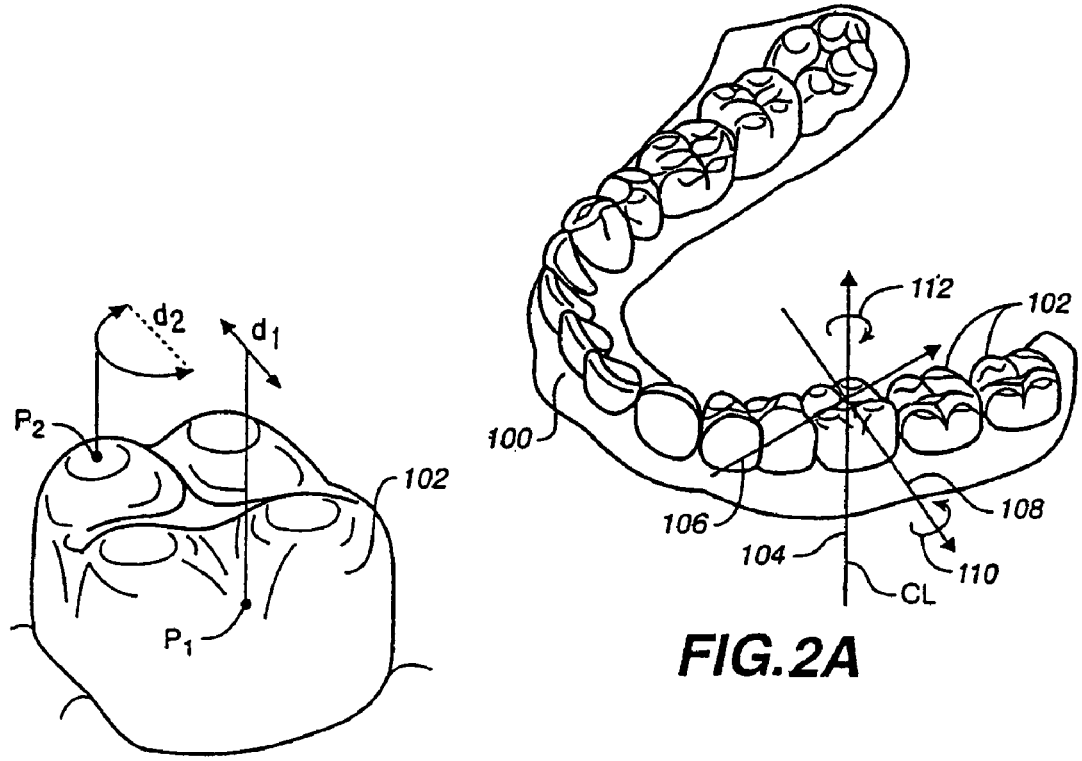
FIG. 2A illustrates in more detail the patient's lower jaw and provides a general indication of how teeth may be moved by the methods and apparatus of the present invention.

Referring now to FIG. 2A, the lower jaw 100 includes a plurality of teeth 102, for example. At least some of these teeth may be moved from an initial tooth arrangement to a final tooth arrangement. As a frame of reference describing how a tooth may be moved, an arbitrary centerline (CL) may be drawn through the tooth 102. With reference to this centerline (CL), each tooth may be moved in orthogonal directions represented by axes 104, 106, and 108 (where 104 is the centerline). The centerline may be rotated about the axis 108 (root angulation) and the axis 104 (torque) as indicated by arrows 110 and 112, respectively. Additionally, the tooth may be rotated about the centerline, as represented by an arrow 114 to FIG. 2A. Thus, all possible free-form motions of the tooth can be performed.

Figure 2B:
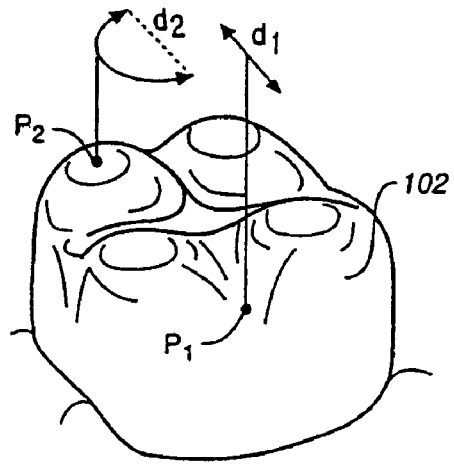
FIG. 2B illustrates a single tooth from FIG. 2A and defines how tooth movement distances are determined.

FIG. 2B shows how the magnitude of any tooth movement may be defined in terms of a maximum linear translation of any point P on a tooth 102. Each point $P_1$ will undergo a cumulative translation as that tooth is moved in any of the orthogonal or rotational directions defined in FIG. 2A. That is, while the point will usually follow a nonlinear path, there is a linear distance between any point in the tooth when determined at any two times during the treatment. Thus, an arbitrary point $P_1$ may in fact undergo a true side-to-side translation as indicated by arrow $d_1$, while a second arbitration point $P_2$ may travel along an arcuate path, resulting in a final translation $d_2$. Many aspects of the present invention are defined in terms of the maximum permissible movement of a point $P_1$ induced on any particular tooth. Such maximum tooth movement, in turn, is defined as the maximum linear translation of that point $P_1$ on the tooth which undergoes the maximum movement for that tooth in any treatment step.

Figure 2C:
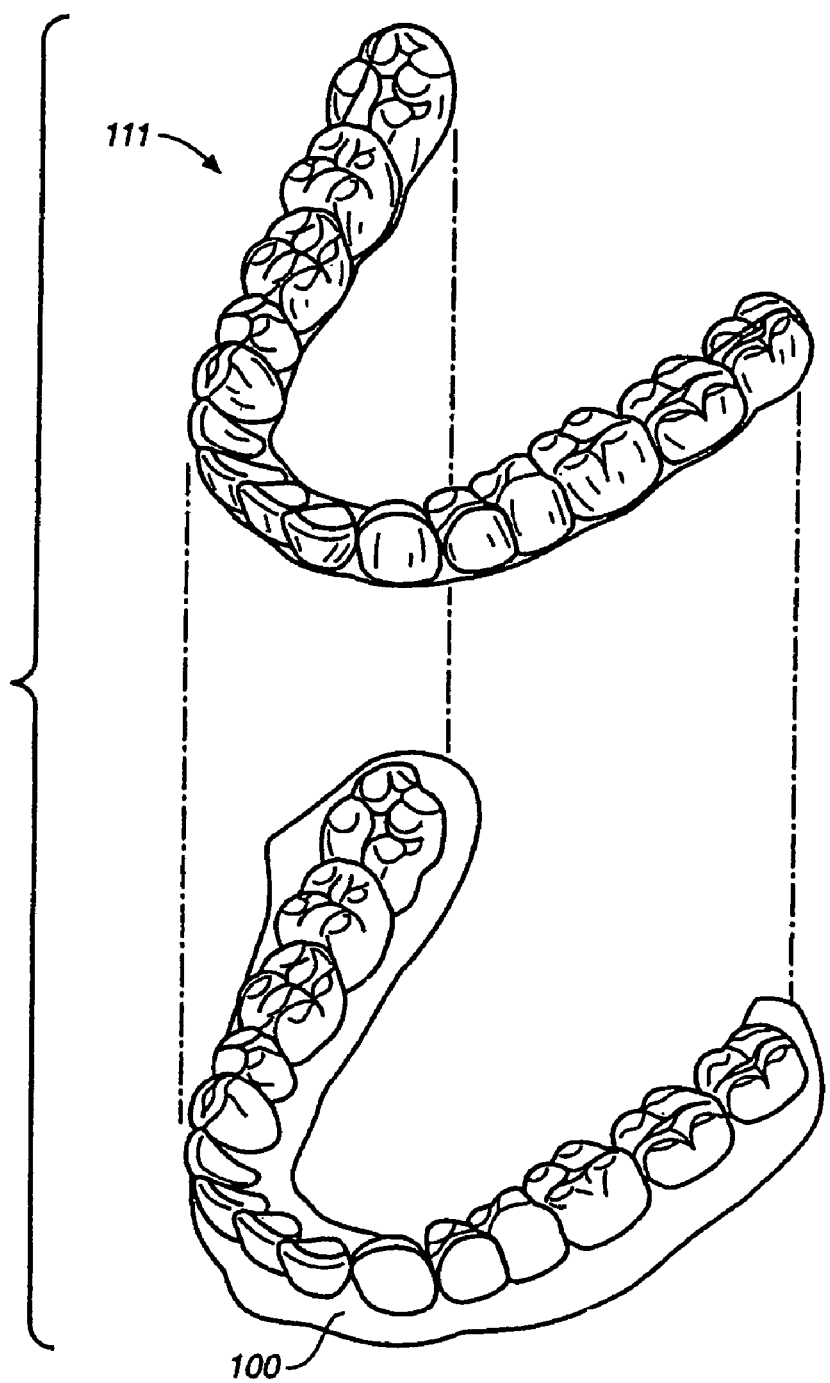
FIG. 2C illustrates the jaw of FIG. 2A together with an incremental position adjustment appliance which has been configured according to the methods and apparatus of the present invention.

FIG. 2C shows one adjustment appliance 111 which is worn by the patient in order to achieve an incremental repositioning of individual teeth in the jaw as described generally above. The appliance is a polymeric shell having a teeth receiving cavity. This is described in U.S. application Ser. No. 09/169,036, filed Oct. 8, 1998, now U.S. Pat. No. 6,450,807, which claims priority from U.S. application Ser. No. 08/947,080, filed Oct. 8, 1997, now U.S. Pat. No. 5,975,893, which in turn claims priority from provisional application No. 60/050,352, filed Jun. 20, 1997 (collectively the "prior applications"), the full disclosures of which are incorporated by reference.

As set forth in the prior applications, each polymeric shell may be configured so that its tooth receiving cavity has a geometry corresponding to an intermediate or final tooth arrangement intended for the appliance. The patient's teeth are repositioned from their initial tooth arrangement to a final tooth arrangement by placing a series of incremental position adjustment appliances over the patient's teeth. The adjustment appliances are generated at the beginning of the treatment, and the patient wears each appliance until the pressure of each appliance on the teeth can no longer be felt. At that point, the patient replaces the current adjustment appliance with the next adjustment appliance in the series until no more appliances remain. Conveniently, the appliances are generally not affixed to the teeth and the patient may place and replace the appliances at any time during the procedure. The final appliance or several appliances in the series may have a geometry or geometries selected to overcorrect the tooth arrangement, i.e., have a geometry which would (if fully achieved) move individual teeth beyond the tooth arrangement which has been selected as the "final." Such overcorrection may be desirable in order to offset potential relapse after the repositioning method has been terminated, i.e., to permit some movement of individual teeth back toward their precorrected positions. Overcorrection may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

The polymeric shell 111 can fit over all teeth present in the upper or lower jaw. Often, only certain one(s) of the teeth will be repositioned while others of the teeth will provide a base or an anchor region for holding the appliance 111 in place as the appliance 111 applies a resilient repositioning force against the tooth or teeth to be repositioned. In complex cases, however, multiple teeth may be repositioned at some point during the treatment. In such cases, the teeth which are moved can also serve as a base or anchor region for holding the repositioning appliance.

The polymeric appliance 111 of FIG. 2C may be formed from a thin sheet of a suitable elastomeric polymer, such as Tru Tain 0.03 in, thermal forming dental material, available from Tru Tain Plastics, Rochester, Minn. Usually, no wires or other means will be provided for holding the appliance in place over the teeth. In some cases, however, it will be desirable or necessary to provide individual anchors on teeth with corresponding receptacles or apertures in the appliance 111 so that the appliance can apply an upward force on the tooth which would not be possible in the absence of such an anchor.

FIG. 3 shows a process 200 for producing the incremental position adjustment appliances for subsequent use by a patient to reposition the patient's teeth. As a first step, an initial digital data set (IDDS) representing an initial tooth arrangement is obtained (step 202).

In some implementations, the IDDS includes data obtained by scanning a physical model of the patient's teeth, such as by scanning a positive impression or a negative impression of the patient's teeth with a laser scanner or a destructive scanner. The positive and negative impression may be scanned while interlocked with each other to provide more accurate data. The initial digital data set also may include volume image data of the patient's teeth, which the computer can convert into a 3D geometric model of the tooth surfaces, for example using a conventional marching cubes technique. In some embodiments, the individual tooth models include data representing hidden tooth surfaces, such as roots imaged through x-ray, CT scan, or MRI techniques. Tooth roots and hidden surfaces also can be extrapolated from the visible surfaces of the patient's teeth. The IDDS is then manipulated using a computer having a suitable graphical user interface (GUI) and software appropriate for viewing and modifying the images. More specific aspects of this process will be described in detail below.

Individual tooth and other components may be segmented or isolated in the model to permit their individual repositioning or removal from the digital model. After segmenting or isolating the components, the user will often reposition the tooth in the model by following a prescription or other written specification provided by the treating professional. Alternatively, the user may reposition one or more teeth based on a visual appearance or based on rules and algorithms programmed into the computer. Once the user is satisfied, the final teeth arrangement is incorporated into a final digital data set (FDDS) (step 204).

In step 204, final positions for the upper and lower teeth in a masticatory system of a patient are determined by generating a computer representation of the masticatory system. An occlusion of the upper and lower teeth is computed from the computer representation; and a functional occlusion is computed based on interactions in the computer representation of the masticatory system. The occlusion may be determined by generating a set of ideal models of the teeth. Each ideal model in the set of ideal models is an abstract model of idealized teeth placement which is customized to the patient's teeth, as discussed below. After applying the ideal model to the computer representation, the position of the teeth is optimized to fit the ideal model. The ideal model may be specified by one or more arch forms, or may be specified using various features associated with the teeth.

The FDDS is created by following the orthodontists' prescription to move the teeth in the model to their final positions. In one embodiment, the prescription is entered into a computer, which automatically computes the final positions of the teeth. In alternative other embodiments, a user moves the teeth into their final positions by independently manipulating one or more teeth while satisfying the constraints of the prescription. Various combinations of the above described techniques may also be used to arrive at the final tooth positions.

One method for creating the FDDS involves moving the teeth in a specified sequence. First, the centers of each tooth model may be aligned using a number of methods. One method is a standard arch. Then, the teeth models are rotated until their roots are in the proper vertical position. Next, the teeth models are rotated around their vertical axis into the proper orientation. The teeth models are then observed from the side, and translated vertically into their proper vertical position. Finally, the two arches are placed together, and the teeth models moved slightly to ensure that the upper and lower arches properly mesh together. The meshing of the upper and lower arches together is visualized using a collision detection process to highlight the contacting points of the teeth.

Based on both the IDDS and the FDDS, a plurality of intermediate digital data sets (INTDDS) are defined to correspond to incrementally adjusted appliances (step 206). Finally, a set of incremental position adjustment appliances are produced based on the INTDDS and the FDDS (step 208).

After the teeth and other components have been placed or removed to produce a model of the final tooth arrangement, it is necessary to generate a treatment plan which produces a series of INTDDS's and FDDS as described previously. To produce these data sets, it is necessary to define or map the movement of selected individual teeth from the initial position to the final position over a series of successive steps. In addition, it may be necessary to add other features to the data sets in order to produce desired features in the treatment appliances. For example, it may be desirable to add wax patches to the image in order to define cavities or recesses for particular purposes, such as to maintain a space between the appliance and particular regions of the teeth or jaw in order to reduce soreness of the gums, avoid periodontal problems, allow for a cap, and the like. Additionally, it will often be necessary to provide a receptacle or aperture intended to accommodate an anchor which is to be placed on a tooth in order to permit the tooth to be manipulated in a manner that requires the anchor, e.g., to be lifted relative to the jaw.

In the manner discussed above, information on how the patient's teeth should move from an initial, untreated state to a final, treated state is used to generate a prescription, or treatment plan. The prescription takes into consideration the following:

1. Initial Position: a detailed description of the initial malocclusion.
2. Final Position: a detailed description of treatment goals for the patient.
3. Movement: a detailed, sequential description of how the patient's teeth should be moved in order to accomplish the desired goals for final placement.

1. Initial Position. The initial position section describes in detail the patient's malocclusion. Considerations include:
  1. Crowding
  2. Spacing
  3. Extraction
  4. Stripping Additionally, considerations for the Final Position discussed below may also be used.

2. Final Position. This section is a detailed description of final position objectives and treatment goals—both static and functional. These considerations include
  1. Overjet
  2. Overbite
  3. Midlines
  4. Functional Occlusion
  5. Classification
  6. Torque
  7. Tip
  8. Rotations
  9. Lingual/Palatal
  10. Buccal/Facial
  11. Intercuspation
  12. Initial Position of the Occlusion—CR/CO Considerations
  13. Interarch Issues
  14. Intra-arch Issues
  15. Space 3. Movement. The movement section specifies an order in moving the patient's teeth in order to achieve the goals for final placement. In this process, the orthodontist has precise control over which teeth the orthodontist wants to move and which teeth to anchor (not move), thereby breaking the treatment down into discrete stages. The movement order information is captured for both the upper and the lower arches.

At each stage, major and minor tooth movements are analyzed. Major movements usually occur at the beginning of a tooth's movement. Minor movements usually occur as "detailing" movements that occur toward the end of treatment. On average, each aligner should be able to accomplish movements of about 0.25-0.33 mm and to rotate about 5-10 degrees within a 2-week period. However, biologic variability, patient and clinician preferences are also taken into consideration. Additionally, various movements such as distalization, tip, and torque can have separate parameters.

Based on these considerations, a plan is generated for moving teeth. FIG. 4 illustrates a process 300 for generating tooth movements while minimizing teeth indices, as discussed in copending U.S. application Ser. No. 09/169,034, now U.S. Pat. No. 6,471,511, the content of which is hereby incorporated by reference. First, the process 300 automatically or, with human assistance, identifies various features associated with each tooth to arrive at a model of the teeth (step 302). An ideal model set of teeth is then generated either from casts of the patient's teeth or from patients with a known acceptable occlusion (step 303).

From step 302, the process 300 positions the model of the teeth in its approximate final position based on a correspondence of features to the ideal model (step 304). In that step, each tooth model is moved so that its features are aligned to the features of a corresponding tooth in the ideal model. The features may be based on cusps, fossae, ridges, distance-based metrics, or shape-based metrics. Shape-based metrics may be expressed as a function of the patient's arches, among others.

Next, the process 300 computes an orthodontic/occlusion index (step 306). One index which may be used is the PAR (Peer Assessment Rating) index. In addition to PAR, other metrics such as shape-based metrics or distance-based metrics may be used. The PAR index identifies how far a tooth is from a good occlusion. A score is assigned to various occlusal traits which make up a malocclusion. The individual scores are summed to obtain an overall total, representing the degree a case deviates from normal alignment and occlusion. Normal occlusion and alignment is defined as all anatomical contact points being adjacent, with a good intercuspal mesh between upper and lower buccal teeth, and with nonexcessive overjet and overbite.

In PAR, a score of zero would indicate good alignment, and higher scores would indicate increased levels of irregularity. The overall score is recorded on pre and posttreatment dental casts. The difference between these scores represents the degree of improvement as a result of orthodontic intervention and active treatment. The eleven components of the PAR Index are: upper right segment; upper anterior segment; upper left segment; lower right segment; lower anterior segment; lower left segment; right buccal occlusion; overjet; overbite; centerline; and left buccal occlusion. In addition to the PAR index, other indices may be based on distances of the features on the tooth from their ideal positions or ideal shapes.

From step 306, the process 300 determines whether additional index-reducing movements are possible (step 308). Here, all possible movements are attempted, including small movements along each major axis as well as small movements with minor rotations. An index value is computed after each small movement and the movement with the best result is selected. In this context, the best result is the result that minimizes one or more metrics such as PAR-based metrics, shape-based metrics or distance-based metrics. The optimization may use a number of techniques, including simulated annealing technique, hill climbing technique, best-first technique, Powell method, and heuristics technique, among others. Simulated annealing techniques may be used where the index is temporarily increased so that another path in the search space with a lower minimum may be found. However, by starting with the teeth in an almost ideal position, any decrease in the index should converge to the best result.

In step 308, if the index can be optimized by moving the tooth, incremental index-reducing movement inputs are added (step 310) and the process loops back to step 306 to continue computing the orthodontic/occlusion index. Alternatively, in the event that the index cannot be further optimized, the process 300 exits (step 312).

In generating the index reducing movements of step 310, the process considers a set of movement constraints which affect the tooth path movement plan. In one embodiment, movement information for about fifty discrete stages is specified. Each stage represents a single aligner, which is expected to be replaced about every two weeks. Thus, each stage represents about a two-week period. In one embodiment, a two-dimensional array is used to track specific movements for each tooth at a specific period of time. One dimension of this array relates to teeth identification, while the second dimension relates to the time periods or stages. Considerations on when a tooth may be moved include the following:

1. Mesial
2. Distal
3. Buccal/Facial
4. Lingual/Palatial
5. Expansion
6. Space
7. Teeth moving past each other
8. Intrusion
9. Extrusion
10. Rotations
11. Which teeth are moving when?
12. Which teeth move first?
13. Which teeth need to be moved before others are moved?
14. What movements are easily done?
15. Anchorage
16. The orthodontist user's philosophy on distalization of molars and minor expansion in adults In one embodiment, the user can change the number of desired treatment stages from the initial to the target states of the teeth. Any component that is not moved is assumed to remain stationary, and thus its final position is assumed to be the same as the initial position (likewise for all intermediate positions, unless one or more key frames are defined for that component).

The user may also specify "key frames" by selecting an intermediate state and making changes to component position(s). In some embodiments, unless instructed otherwise, the software automatically linearly interpolates between all user-specified positions (including the initial position, all key frame positions, and the target position). For example, if only a final position is defined for a particular component, each subsequent stage after the initial stage will simply show the component an equal linear distance and rotation (specified by a quaternion) closer to the final position. If the user specifies two key frames for that component, the component will "move" linearly from the initial position through different stages to the position defined by the first key frame. It will then move, possibly in a different direction, linearly to the position defined by the second key frame. Finally, it will move, possibly in yet a different direction, linearly to the target position.

These operations may be done independently to each component, so that a key frame for one component will not affect another component, unless the other component is also moved by the user in that key frame. One component may accelerate along a curve between one pair of stages (e.g., stages 3 and 8 in a treatment plan having that many stages), while another moves linearly between another pair of stages (e.g., stages 1 to 5), and then changes direction suddenly and slows down along a linear path to a later stage (e.g., stage 10). This flexibility allows a great deal of freedom in planning a patient's treatment.

In some implementations, non-linear interpolation is used instead of or in addition to linear interpolation to construct a treatment path among key frames. In general, a non-linear path, such as a spline curve, created to fit among selected points is shorter than a path formed from straight line segments connecting the points. A "treatment path" describes the transformation curve applied to a particular tooth to move the tooth from its initial position to its final position. A typical treatment path includes some combination of rotational and translational movement of the corresponding tooth, as described above.

FIG. 5 shows step 310 in more detail. Initially, a first tooth is selected (step 311). Next, constraints associated with the tooth are retrieved for the current stage or period (step 312). Thus, for the embodiment which keeps a two-dimensional array to track specific movements for each tooth at a specific period of time, the tooth identification and the time period or stage information are used to index into the array to retrieve the constraints associated with the current tooth.

Next, a tooth movement plan which takes into consideration the constraints is generated (step 313). The process of FIG. 5 then detects whether the planned movements would cause collisions with neighboring teeth (step 314). The collision detection process determines if any of the geometries describing the tooth surfaces intersect. If there are no obstructions, the space is considered free; otherwise it is obstructed. Suitable collision detection algorithms are discussed in more detail below.

If a collision occurs, a "push" vector is created to shift the path of the planned movement (step 315). Based on the push vector, the current tooth "bounces" from the collision and a new tooth movement is generated (step 316). From step 314 or 316, the movement of the current tooth is finalized.

Next, the process of FIG. 5 determines whether tooth movement plans have been generated for all teeth (step 317), and if so, the process exits. Alternatively, the next tooth in the treatment plan is selected (318), and the process of FIG. 5 loops back to step 312 to continue generating tooth movement plans.

The resulting final path consists of a series of vectors, each of which represents a group of values of the interpolation parameters of the translational and rotational components of the transformations of the moving teeth. Taken together, these constitute a schedule of tooth movement which avoids tooth to tooth interferences. Pseudo code for generating the tooth path in view of specified constraints is shown below:

For each tooth path model
For each path increment
Load constrains associated with each tooth
Move the tooth in view of constraint
Perform tooth collision detection
If collision occurs, for associated colliding teeth create "push" vector and "bounce" back from collision to avoid collision.

FIG. 6 is a flow chart of a computer-implemented process for generating non-linear treatment paths along which a patient's teeth will travel during treatment. The non-linear paths usually are generated automatically by computer program, in some cases with human assistance. The program receives as input the initial and final positions of the patient's teeth and uses this information to select intermediate positions for each tooth to be moved (step 1600). The program then applies a conventional spline curve calculation algorithm to create a spline curve connecting each tooth's initial position to the tooth's final position (step 1602). In many situations, the curve is constrained to follow the shortest path between the intermediate positions. The program then samples each spline curve between the intermediate positions (step 1604) and applies the collision detection algorithm to the samples (step 1606). If any collisions are detected, the program alters the path of at least one tooth in each colliding pair by selecting a new position for one of the intermediate steps (step 1608) and creating a new spline curve (1602). The program then samples the new path (1604) and again applies the collision detection algorithm (1606). The program continues in this manner until no collisions are detected. The routine then stores the paths, e.g., by saving the coordinates of each point in the tooth at each position on the path in an electronic storage device, such as a hard disk (step 1610).

The path-generating program, whether using linear or non-linear interpolation, selects the treatment positions so that the tooth's treatment path has approximately equal lengths between each adjacent pair of treatment steps. The program also avoids treatment positions that force portions of a tooth to move with more than a given maximum velocity.

Orthodontic constraints that may be applied by the path-generating program include the minimum and maximum distances allowed between adjacent teeth at any given time, the maximum linear or rotational velocity at which a tooth should move, the maximum distance over which a tooth should move between treatment steps, the shapes of the teeth, the characteristics of the tissue and bone surrounding the teeth (e.g., ankylose teeth cannot move at all), and the characteristics of the aligner material (e.g., the maximum distance that the aligner can move a given tooth over a given period of time). For example, the patient's age and jaw bone density may dictate certain "safe limits" beyond which the patient's teeth should not be forced to move. In general, a gap between two adjacent, relatively vertical and non-tipped central and lateral teeth should not close by more than about 1 mm every seven weeks. The material properties of the orthodontic appliance also limit the amount by which the appliance can move a tooth. For example, conventional retainer materials usually limit individual tooth movement to approximately 0.5 mm between treatment steps. The constraints have default values that apply unless patient-specific values are calculated or provided by a user. Constraint information is available from a variety of sources, including text books and treating clinicians.

In selecting the intermediate positions for each tooth, the path-generating program invokes the collision detection program to determine whether collisions will occur along the chosen paths. The program also inspects the patient's occlusion at each treatment step along the path to ensure that the teeth align to form an acceptable bite throughout the course of treatment. If collisions or an unacceptable bite will occur, or if a required constraint cannot be satisfied, the program iteratively alters the offending tooth path until all conditions are met. The virtual articulator described above is one tool for testing bite occlusion of the intermediate treatment positions.

As shown in FIG. 7, once the path-generating program has established collision-free paths for each tooth to be moved, the program calls an optimization routine that attempts to make the transformation curve for each tooth between the initial and final positions more linear. The routine begins by sampling each treatment path at points between treatment steps (step 1702), e.g., by placing two sample points between each treatment step, and calculating for each tooth a more linear treatment path that fits among the sample points (step 1704). The routine then applies the collision detection algorithm to determine whether collisions result from the altered paths (step 1706). If so, the routine resamples the altered paths (step 1708) and then constructs for each tooth an alternative path among the samples (step 1710). The routine continues in this manner until no collisions occur (step 1712).

In some embodiments, as alluded to above, the software automatically computes the treatment path, based upon the IDDS and the FDDS. This is accomplished using a path scheduling algorithm which determines the rate at which each component, i.e., each tooth, moves along the path from the initial position to the final position. The path scheduling algorithm determines the treatment path while avoiding "round-tripping," i.e., while avoiding moving a tooth along a distance greater than absolutely necessary to straighten the teeth. Such motion is highly undesirable, and has potential negative effects on the patient.

One implementation of the path scheduling algorithm attempts first to schedule or stage the movements of the teeth by constraining each tooth to the most linear treatment path between the initial and final positions. The algorithm then resorts to less direct routes to the final positions only if collisions will occur between teeth along the linear paths or if mandatory constraints will be violated. The algorithm applies one of the path-generation processes described above, if necessary, to construct a path for which the intermediate treatment steps do not lie along a linear transformation curve between the initial and final positions. Alternatively, the algorithm schedules treatment paths by drawing upon a database of preferred treatments for exemplary tooth arrangements. This database can be constructed over time by observing various courses of treatment and identifying the treatment plans that prove most successful with each general class of initial tooth arrangements. The path scheduling algorithm can create several alternative paths and present each path graphically to the user. The algorithm provides as output the path selected by the user.

In other implementations, the path scheduling algorithm utilizes a stochastic search technique to find an unobstructed path through a configuration space which describes possible treatment plans. One approach to scheduling motion between two user defined global key frames is described below. Scheduling over a time interval which includes intermediate key frames is accomplished by dividing the time interval into subintervals which do not include intermediate key frames, scheduling each of these intervals independently, and then concatenating the resulting schedules.

A collision or interference detection algorithm employed in one embodiment is based on the algorithm described in SIGGRAPH article, Stefan Gottschalk et al. (1996):

"OBBTree: A Hierarchical Structure for Rapid Interference Detection." The contents of the SIGGRAPH article are herein incorporated by reference.

The algorithm is centered around a recursive subdivision of the space occupied by an object, which is organized in a binary tree like fashion. Triangles are used to represent the teeth in the IDDS. Each node of the tree is referred to as an oriented bounding box (OBB) and contains a subset of triangles appearing in the node's parent. The children of a parent node contain between them all of the triangle data stored in the parent node.

The bounding box of a node is oriented so it tightly fits around all of the triangles in that node. Leaf nodes in the tree ideally contain a single triangle, but can possibly contain more than one triangle. Detecting collisions between two objects involves determining if the OBB trees of the objects intersect. If the OBBs of the root nodes of the trees overlap, the root's children are checked for overlap. The algorithm proceeds in a recursive fashion until the leaf nodes are reached. At this point, a robust triangle intersection routine is used to determine if the triangles at the leaves are involved in a collision.

The collision detection technique described here provides several enhancements to the collision detection algorithm described in the SIGGRAPH article. For example, OBB trees can be built in a lazy fashion to save memory and time. This approach stems from the observation that some parts of the model will never be involved in a collision, and consequently the OBB tree for such parts of the model need not be computed. The OBB trees are expanded by splitting the internal nodes of the tree as necessary during the recursive collision determination algorithm.

Moreover, the triangles in the model which are not required for collision data may also be specifically excluded from consideration when building an OBB tree. For instance, motion may be viewed at two levels. Objects may be conceptualized as "moving" in a global sense, or they may be conceptualized as "moving" relative to other objects. The additional information improves the time taken for the collision detection by avoiding recomputation of collision information between objects which are at rest relative to each other since the state of the collision between such objects does not change.

FIG. 8 illustrates an alternative collision detection scheme, one which calculates a "collision buffer" oriented along a z-axis 1802 along which two teeth 1804, 1806 lie. The collision buffer is calculated for each treatment step or at each position along a treatment path for which collision detection is required. To create the buffer, an x,y plane 1808 is defined between the teeth 1804, 1806. The plane must be "neutral" with respect to the two teeth. Ideally, the neutral plane is positioned so that it does not intersect either tooth. If intersection with one or both teeth is inevitable, the neutral plane is oriented such that the teeth lie, as much as possible, on opposite sides of the plane. In other words, the neutral plane minimizes the amount of each tooth's surface area that lies on the same side of the plane as the other tooth.

In the plane 1808 is a grid of discrete points, the resolution of which depends upon the required resolution for the collision detection routine. A typical high-resolution collision buffer includes a 400×400 grid; a typical low-resolution buffer includes a 20×20 grid. The z-axis 1802 is defined by a line normal to the plane 1808.

The relative positions of the teeth 1804, 1806 are determined by calculating, for each of the points in the grid, the linear distance parallel to the z-axis 1802 between the plane 1808 and the nearest surface of each tooth 1804, 1806. For example, at any given grid point (M,N), the plane 1808 and the nearest surface of the rear tooth 1804 are separated by a distance represented by the value $Z1(M,N)$, while the plane 1808 and the nearest surface of the front tooth 1806 are separated by a distance represented by the value $Z2(M,N)$. If the collision buffer is defined such that the plane 1808 lies at $z=0$ and positive values of z lie toward the back tooth 1804, then the teeth 1804, 1806 collide when $Z1(M,N)=Z2(M,N)$ at any grid point (M,N) on the plane 1808.

FIG. 9 is a flow chart of a collision detection routine implementing this collision buffer scheme. The routine first receives data from one of the digital data sets indicating the positions of the surfaces of the teeth to be tested (step 1900). The routine then defines the neutral x,y-plane (step 1902) and creates the z-axis normal to the plane (step 1904).

The routine then determines for the x,y-position of the first grid point on the plane the linear distance in the z-direction between the plane and the nearest surface of each tooth (step 1906). To detect a collision at that x,y-position, the routine determines whether the z-position of the nearest surface of the rear tooth is less than or equal to the z-position of the nearest surface of the front tooth (step 1908). If so, the routine creates an error message, for display to a user or for feedback to the path-generating program, indicating that a collision will occur (step 1910). The routine then determines whether it has tested all x,y-positions associated with grid points on the plane (step 1912) and, if not, repeats the steps above for each remaining grid point. The collision detection routine is performed for each pair of adjacent teeth in the patient's mouth at each treatment step.

In one embodiment, the system plans a tooth path in accordance with a library of movements. For a given initial position of patient teeth and a final corrected position, the system generates in-between stages by finding the stage positions of each tooth in accordance with a selected movement. FIGS. 10-13 show exemplary movement patterns, namely an X-type movement, an A-type movement, a V-type movement, and an XX-type movement, among others. These exemplary movement patterns will be discussed next.

Figure 10:
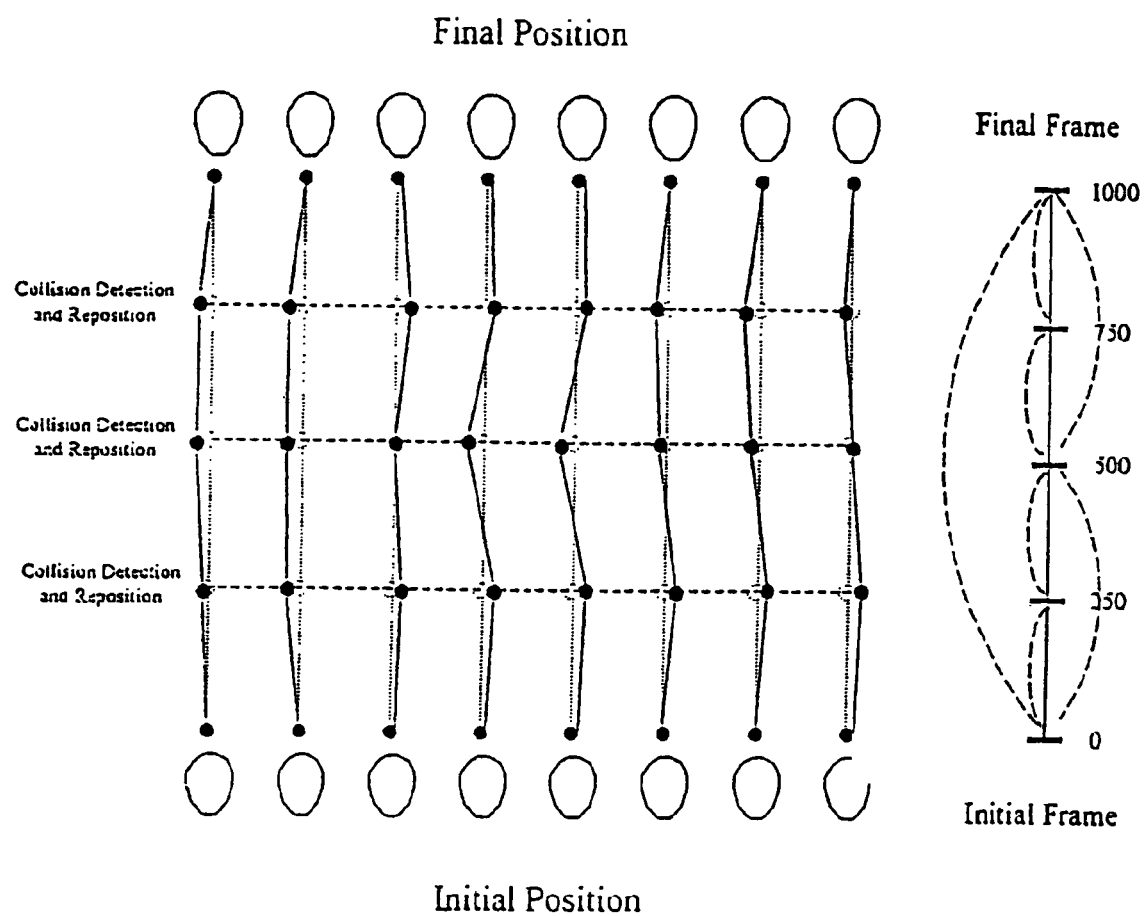
FIG. 10 shows an exemplary X-type movement.

Turning now to FIG. 10, an exemplary X-type movement is shown. The X-type movement is also known as an 'All Equal Movement'. In this movement, all teeth in a given group are moving at the same time. The tooth path is determined by dividing a starting frame containing the teeth into half frames and recursively determines intermediate paths in each half. The recursion stops when the moving distance in each frame meets a given criterion. Once the movements are done, the system adjusts teeth movements so that each frame does not exceed one or more distance constraints.

Figure 11:
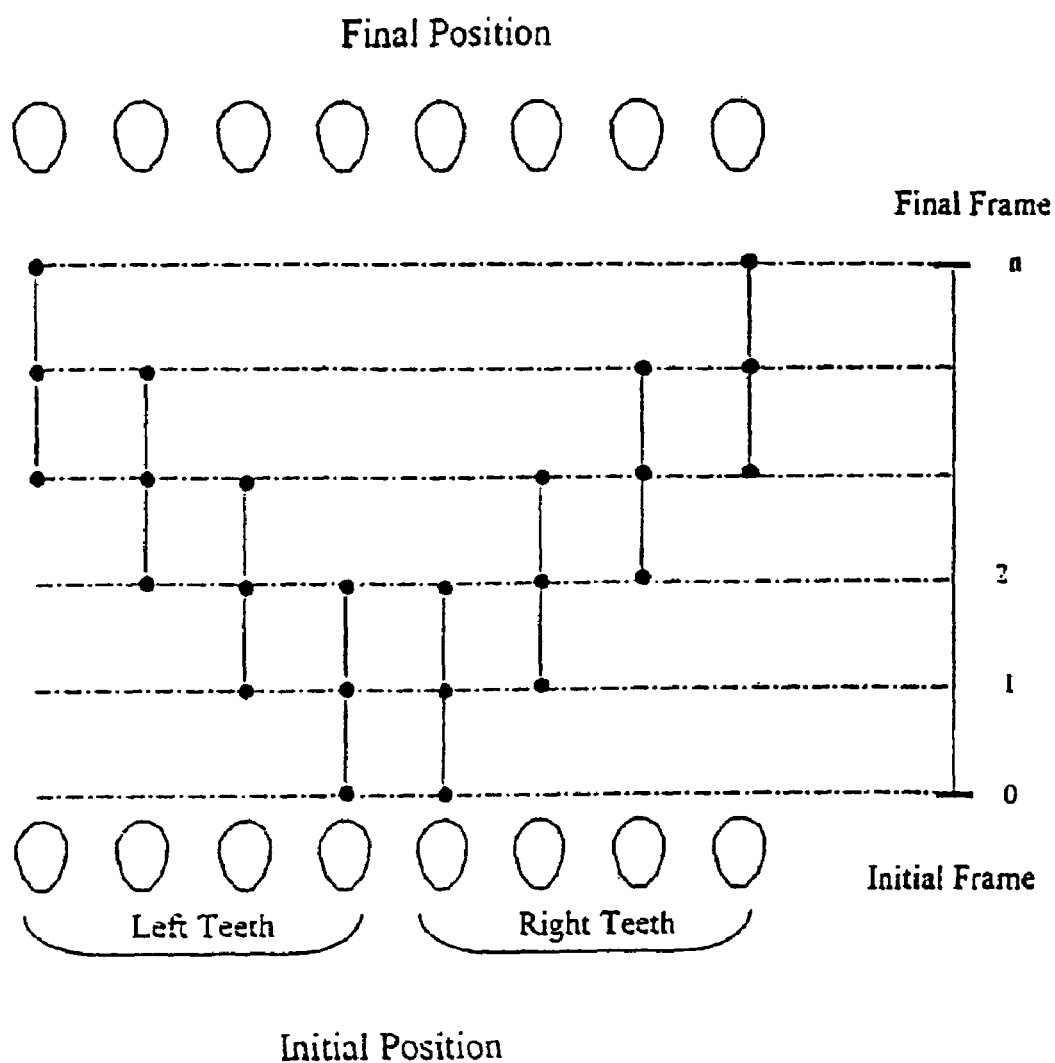
FIG. 11 shows an exemplary A-type movement.

Next, the A-type movement is discussed. In this type of movement, the anterior tooth moves first, followed by the posterior teeth. The movement looks like an A character as the front tooth is moving ahead of the next tooth. In each tooth, the next tooth starts to move when the current tooth reaches midway to the current tooth's goal position. The diagram of the A type movement is shown in FIG. 11.

Figure 12:
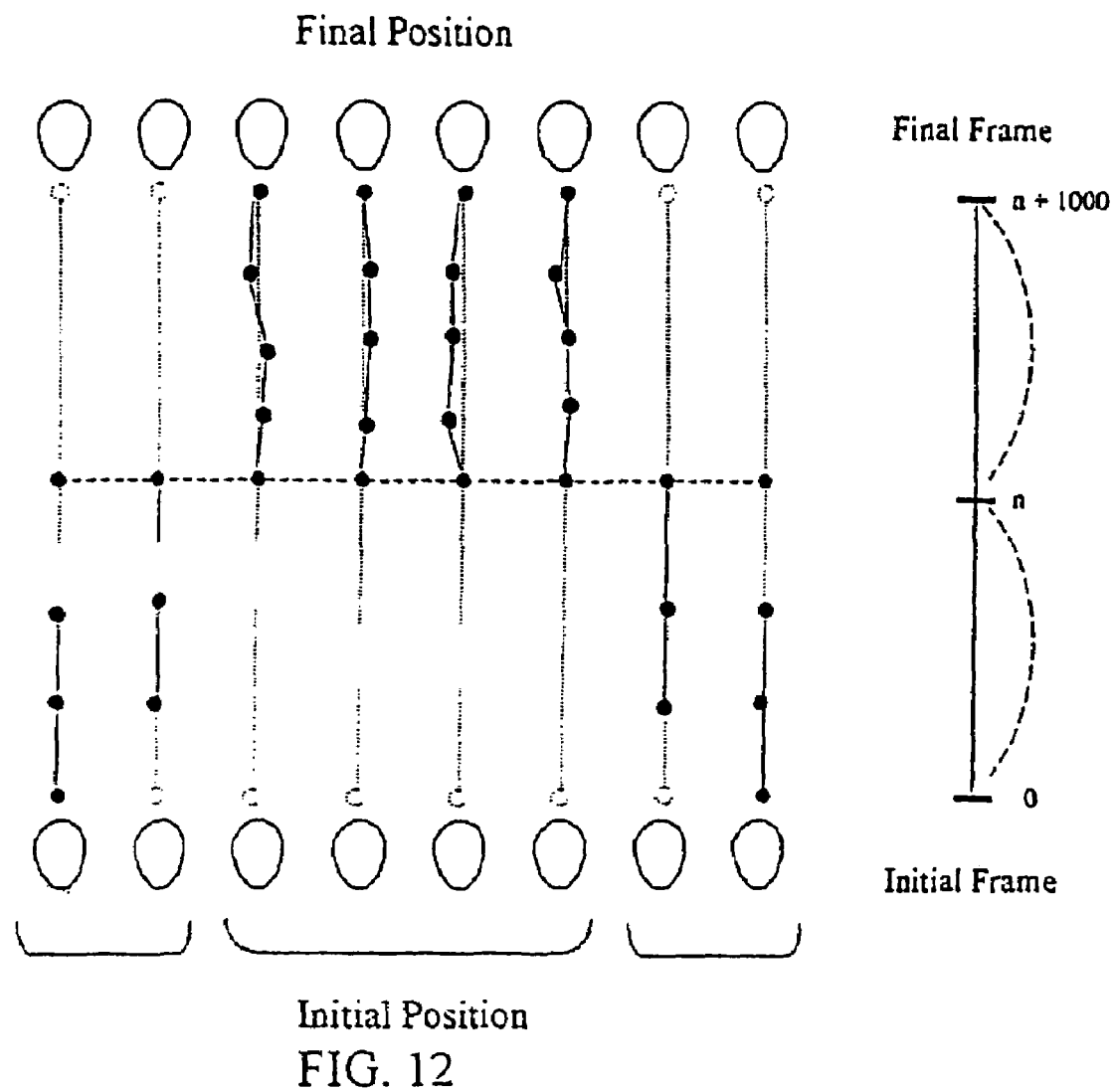
FIG. 12 shows an exemplary V-type movement.

The V-type movement is shown in FIG. 12. Conceptually, the V type movement is reverse of A type movement: the rear teeth move first then the next front teeth follow. In one implementation, a reverse A movement is done for posterior teeth, while the anterior teeth go through an X type movement.

Figure 13:
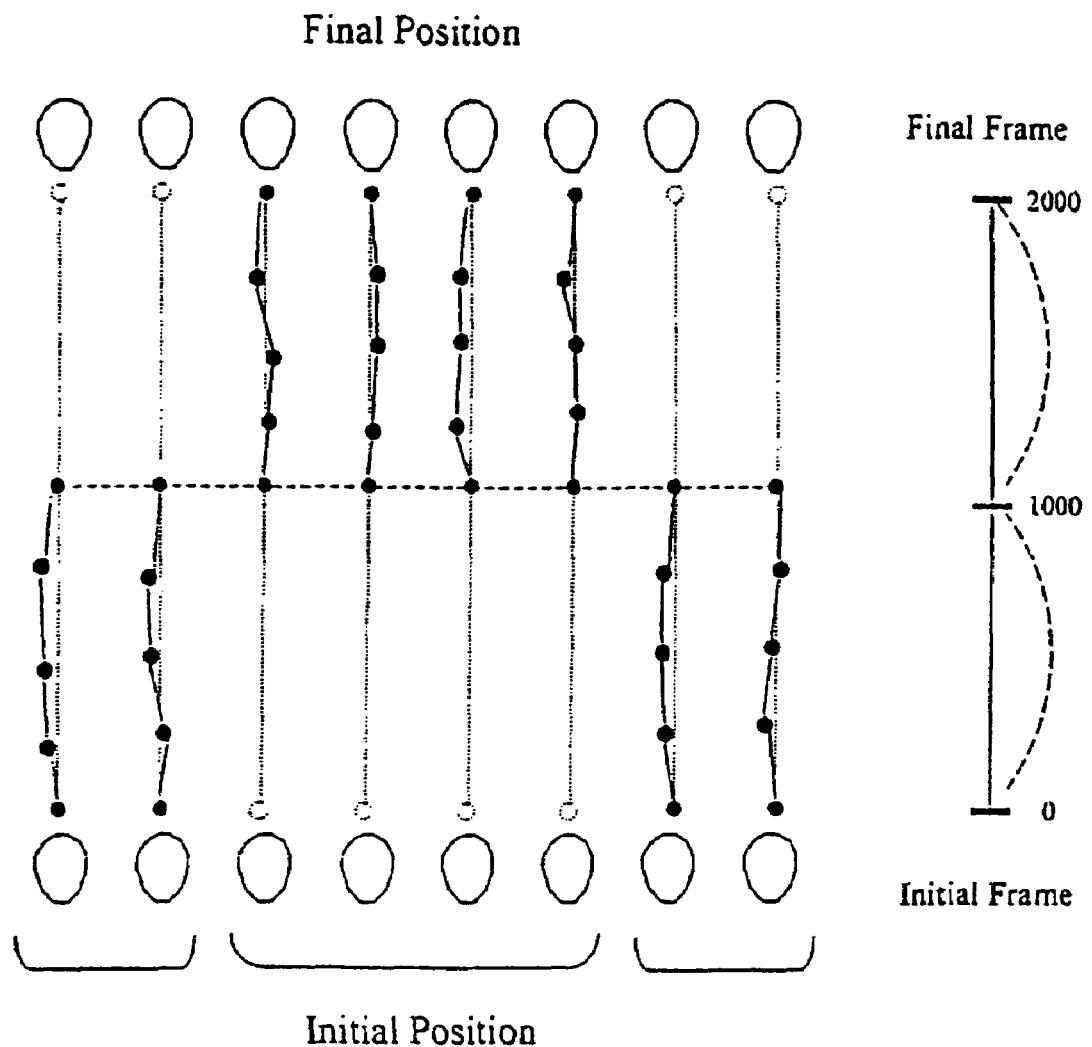
FIG. 13 shows an exemplary XX-type movement.

FIG. 13 shows an XX type movement, which involves two all equal movement. Posterior teeth go through an all equal movement (X-type) first and the anterior teeth go through the all equal movement.

Figure 14:
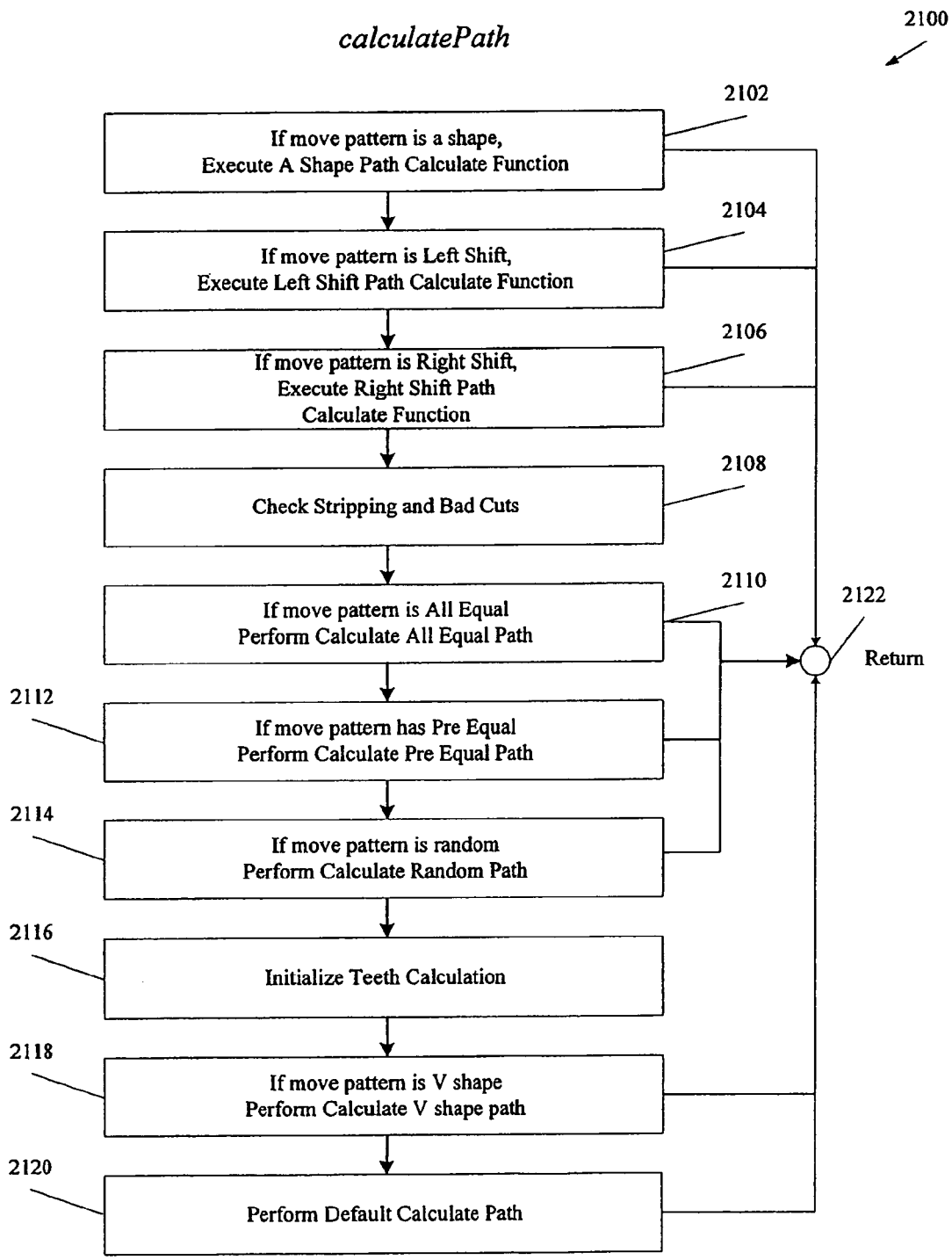
FIG. 14 shows an exemplary process to determine tooth path.

Referring now to FIG. 14, a process 2100 is a top-level routing process that allows a user to select one move pattern from a plurality of move patterns. Before starting, the process 2100 checks various requirements, for example:

Does the jaw have more than one base?
Are the lower jaw teeth attached to upper jaw or vice versa?
Are there any duplicate teeth identifications in the same jaw?
Does each tooth have polygon shape?
Does teeth have high resolution polygon shape?
Does the Z Axis for all teeth point at the same direction?
Are all teeth in their proper order?
Is there any intra arch collision excluding the base at stage 0?
Is there any intra arch collision excluding the base at final stage?

If any of the above checks fail, the process 2100 aborts. Otherwise, the process 2100 determines whether a user has requested an A shape move pattern, and if so, executes an A shaped path calculation (step 2102) and exits (step 2122). If not, the process 2100 further determines whether the user has requested a left shift move pattern and if so, executes a left shift path calculation (step 2104) before exiting (step 2122). From step 2104, if the user had not specified a left shift move pattern, the process 2100 determines whether the user has requested a right shift move pattern and if so, executes a right shift path calculation (step 2106) before exiting (step 2122).

In step 2106, if the move pattern is not a right shift move pattern, the process 2100 checks for stripping and bad cuts (step 2108). The process 2100 also checks whether the user has requested an all equal move pattern, and if so, performs an All Equal path calculation (step 2110) and exits (step 2122). Alternatively, the process 2100 checks whether the user has specified a Pre Equal move pattern, and if so, performs a PreEqual path calculation (step 2112) and then exits (step 2122). Alternatively, if the user specifies a random move pattern, the process 2100 performs a random path calculation (step 2114) and exits (step 2122).

If the move pattern in step 2114 is not a random move pattern, variables used in teeth calculation are initialized (step 2116). The process 2100 also checks whether the move pattern is V shaped pattern, and if so performs a V shaped path calculation (step 2118) and exits (step 2122). Alternatively, the process 2100 executes a default path calculation (step 2120) and exits (step 2122).

In summary, the process 2100 directs the procedure to an appropriate process depending on the move pattern that is specified by the user.

Figure 15:
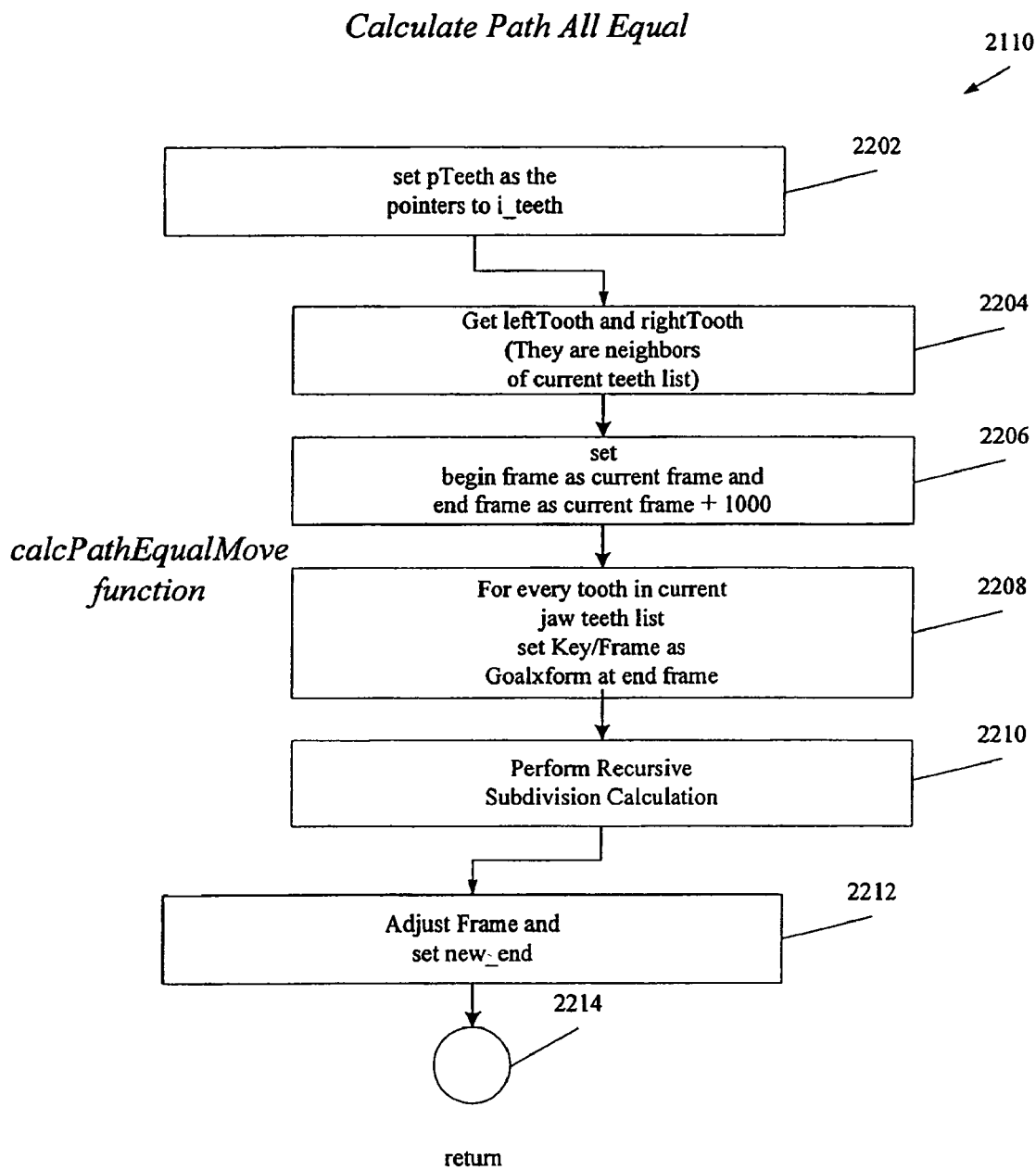
FIG. 15 shows an exemplary process to determine an all-equal path.

Referring now to FIG. 15, the process 2110 for calculating the all equal path is shown. Steps 2202 to 2208 initialize the algorithm. First, the process 2110 sets a pointer to the teeth (step 2202). Next the process 2110 obtains neighbors of the current teeth (step 2204). Next, the process 2110 sets a variable begin_frame as the current frame and a variable end_frame as the current frame plus a predetermined value such as 1000 (step 2206). For every tooth in the current jaw teeth list, the process 2110 sets a transformation goal, or the goal position in 3-D space, as the key frame at end_frame (step 2208). Next, the process 2110 performs a recursive subdivision calculation (step 2210), whose operation is shown in more detail in FIG. 16. The process 2110 then adjusts the frame to refine the frame and set a new end frame (step 2212) before exiting (step 2214). Step 2212 is a finishing process that refines the frames to meet a staging protocol to sequence the tooth movement.

In summary, the process 2110 is the top level of the all equal movement calculation. All teeth move at their respective begin_frame to reach desired goal positions at end_frame. A recursive process calculates the middle frame positions. The all equal movement needs collision detection to find a collision free path, which is done in the process 2240, as described below.

Figure 16:
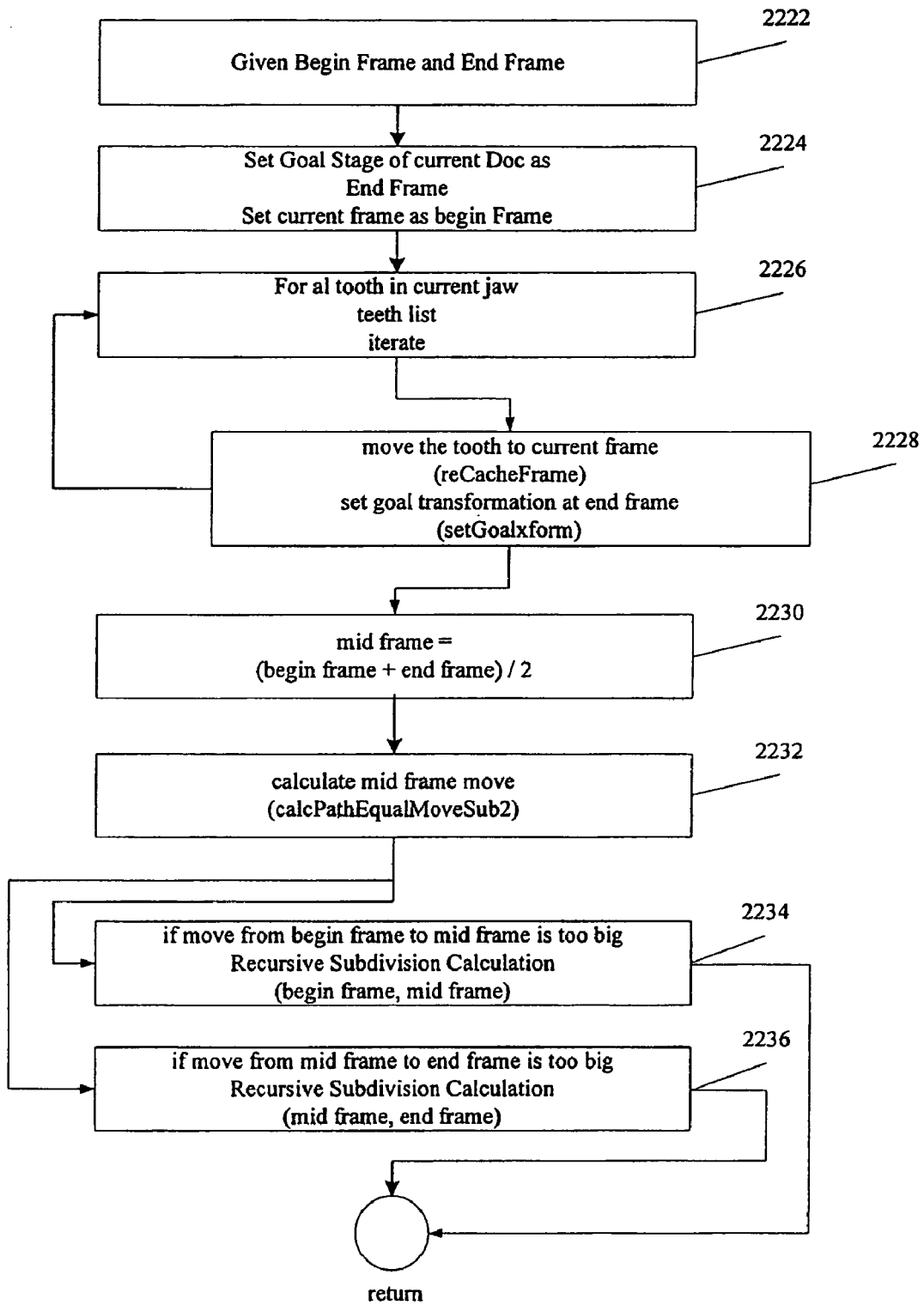
FIG. 16 shows an exemplary process to recursively determine frame movement as used in FIG. 15.

Referring now to FIG. 16, the recursive subdivision calculation process 2210 is shown in more detail. First, the process 2210 receives a begin frame and an end frame (step 2222). Next, the process 2210 puts a goal stage as the end frame, and sets the current frame as the begin frame (step 2224). Next, for all teeth in the current jaw teeth list, the process iterates (step 2226) by moving the tooth to the current frame and setting the goal transformation at the end frame (step 2228). Once all teeth have been processed, the process 2210 computes a mid-frame by averaging the beginning frame and the end frame values (step 2230). Next, the process 2210 calculates the position of the middle frame (step 2232). The process then determines whether the move from the begin frame to the mid-frame exceeds a predetermined size and if so, it recursively invokes the process 2210 (step 2234). Additionally, the process 2210 also determines whether the move from the mid-frame to the end frame exceeds a predetermined limit and if so, recursively invokes itself (step 2236) before exiting.

The process 2210 recursively divides each whole frame in half and calculates the position at the middle frame. The recursion proceeds until the moves of the each half part of the frame falls below a specified criterion. The actual calculation of the position at the middle frame is illustrated in process 2240 below. As the recursion propagates, the collision free positions are determined in the frames.

Figure 17:
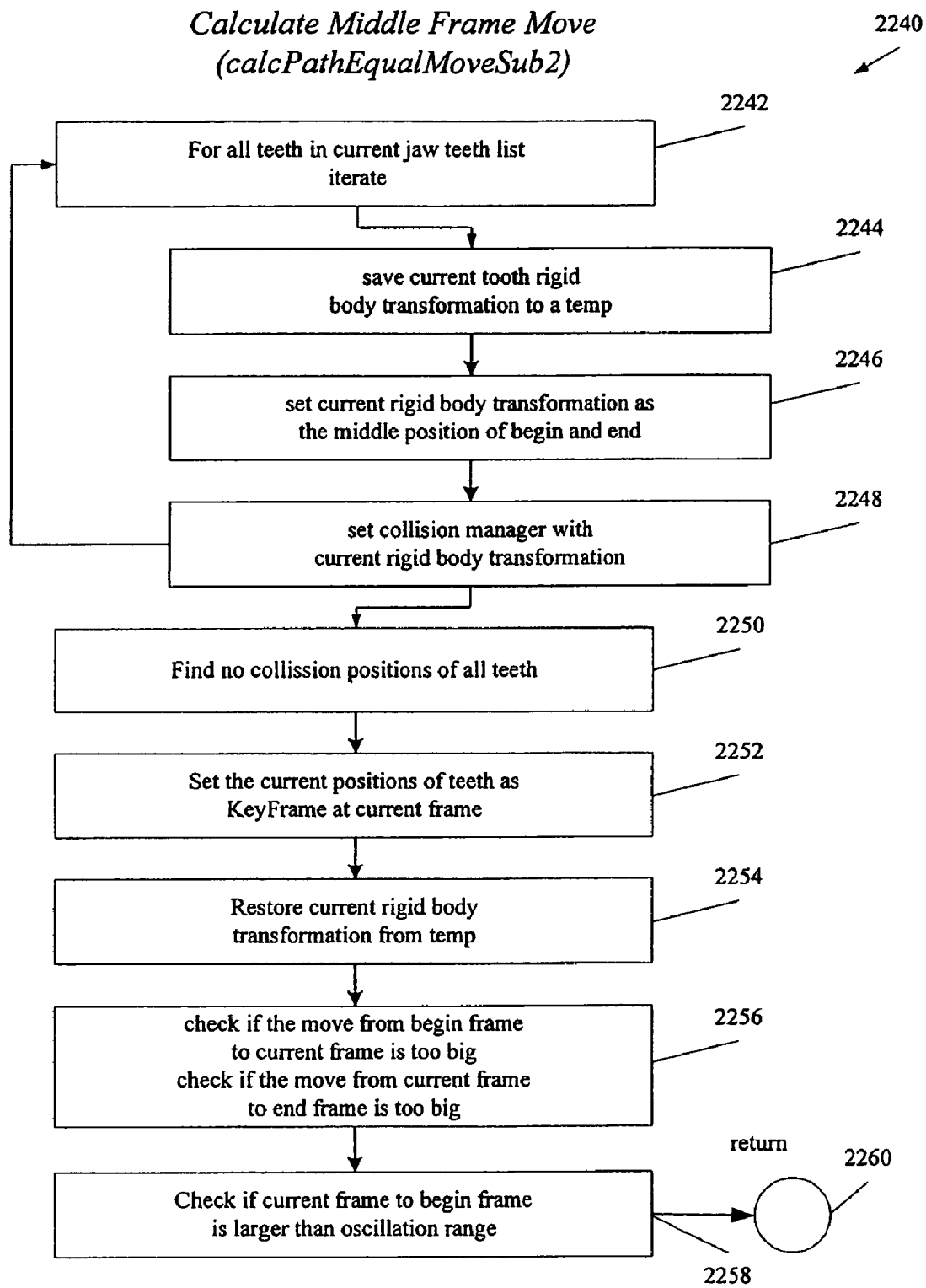
FIG. 17 shows an exemplary process to determine mid-frame movements as used in FIG. 16.

FIG. 17 shows in more detail the process 2240 that computes rigid body transforms for teeth positions at the middle frame. The process 2240 finds collision free positions for all teeth at a given middle frame, and then sets the position to the key frame. For all teeth in the current jaw teeth list, steps 2242-2248 are performed. First, the current tooth rigid body transformation is saved to a temporary variable (step 2244). Next, the current rigid body transformation is set at the middle position for the beginning and the end of the transformation (step 2246). Next, step 2248 sets the current rigid body transformation, the current position, to the collision manager for the process 2250. Steps 2242-2248 are repeated for all teeth in the current jaw. Steps 2242 to 2248 set all teeth in their middle frame positions in a collision manager before triggering a collision detection analysis.

Then, step 2250 triggers the collision detection analysis and moves teeth to collision-free positions. Next, the process 2240 sets the current collision free position as the key frame (step 2252). Next, the process 2240 restores the current rigid body transformation from the temporary variable (step 2254). The process 2240 then checks whether to move from the begin frame to the current frame exceeds a predetermined limit and also checks if the move from the current frame to the end frame exceeds a second predetermined limit (step 2256). The process 2240 also checks whether the current frame to the begin frame exceeds an oscillation range (step 2258). After performing these checks, the process of FIG. 17 exits (step 2260).

In summary, process 2240 finds collision free positions of teeth at the middle of current begin and end frames and then checks the termination criteria.

Figure 18:
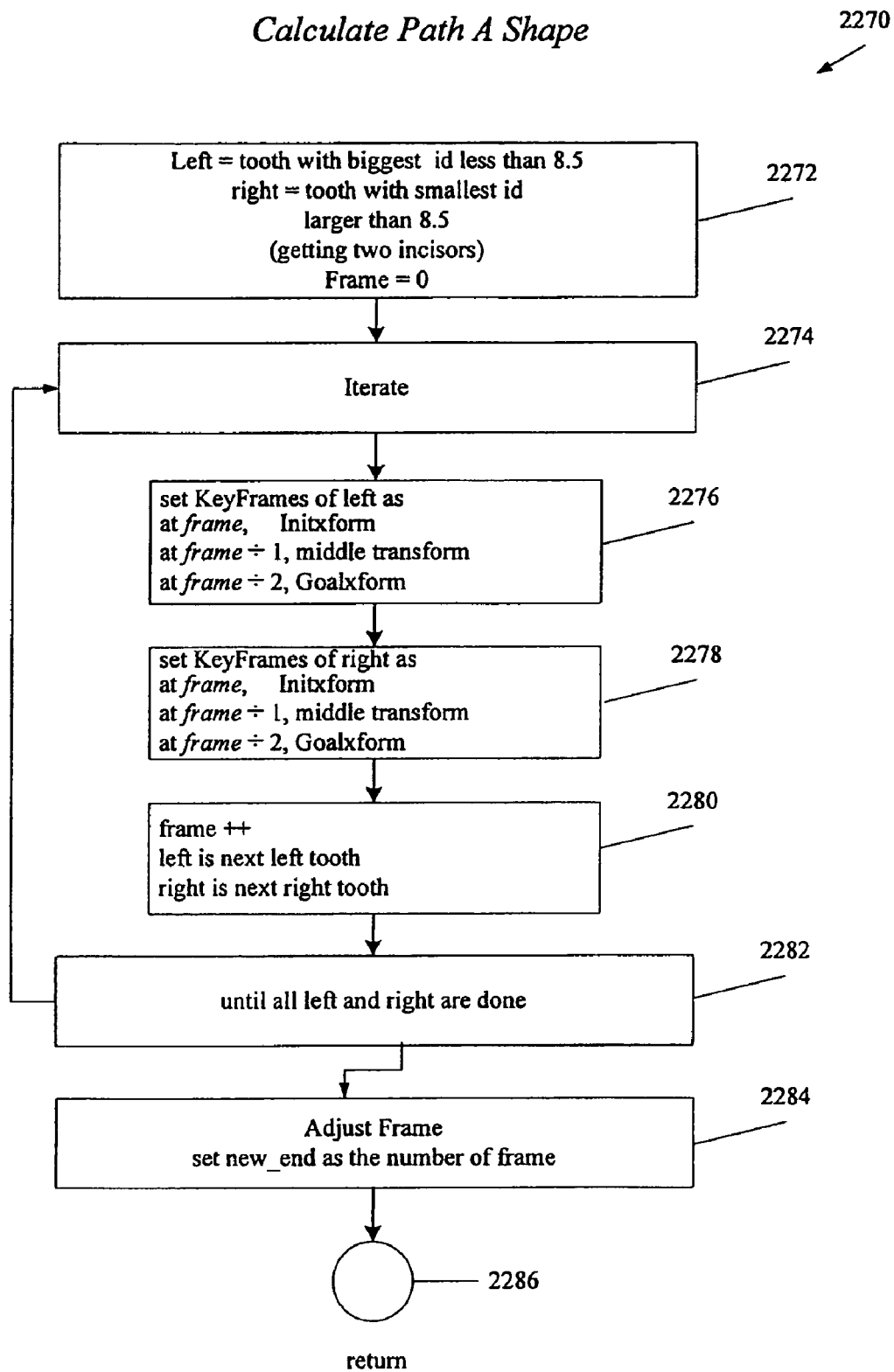
FIG. 18 shows an exemplary process to determine an A-shape path.

FIG. 18 shows a process 2270 for calculating paths for an A-shaped movement. First, the process 2270 determines a left value as being the tooth with the biggest identifier that is below a predetermined value (in this case, 8.5). The right tooth is also selected as the tooth with the smallest identification value larger than the predetermined value. The net effect of this is to obtain two incisor teeth (step 2272).

Next, the process 2270 finds the frame moves iterating tooth by tooth from the incisors to the last molars 2274-2282. First, the process 2276 sets key frames for a left tooth. For the current frame, the key frame is set to an initial transform (initial position), and for the next frame (current frame+1), the key frame is set to the middle transform. For the subsequent frame (current frame+2), the key frame is set to the goal transform (step 2276). The same procedure is applied to a right tooth (step 2278). Next, the frame is incremented and the left tooth becomes the next left tooth and the right tooth becomes the next right tooth (step 2280).

In the above manner, all teeth will move in three frames, and the move will start from incisor teeth and propagates toward posterior teeth. Upon exiting the iterations of steps 2274-2282, the process 2270 adjusts the frames and sets the new end value as the number of the frame (step 2284) and exits (step 2286).

Figure 19:
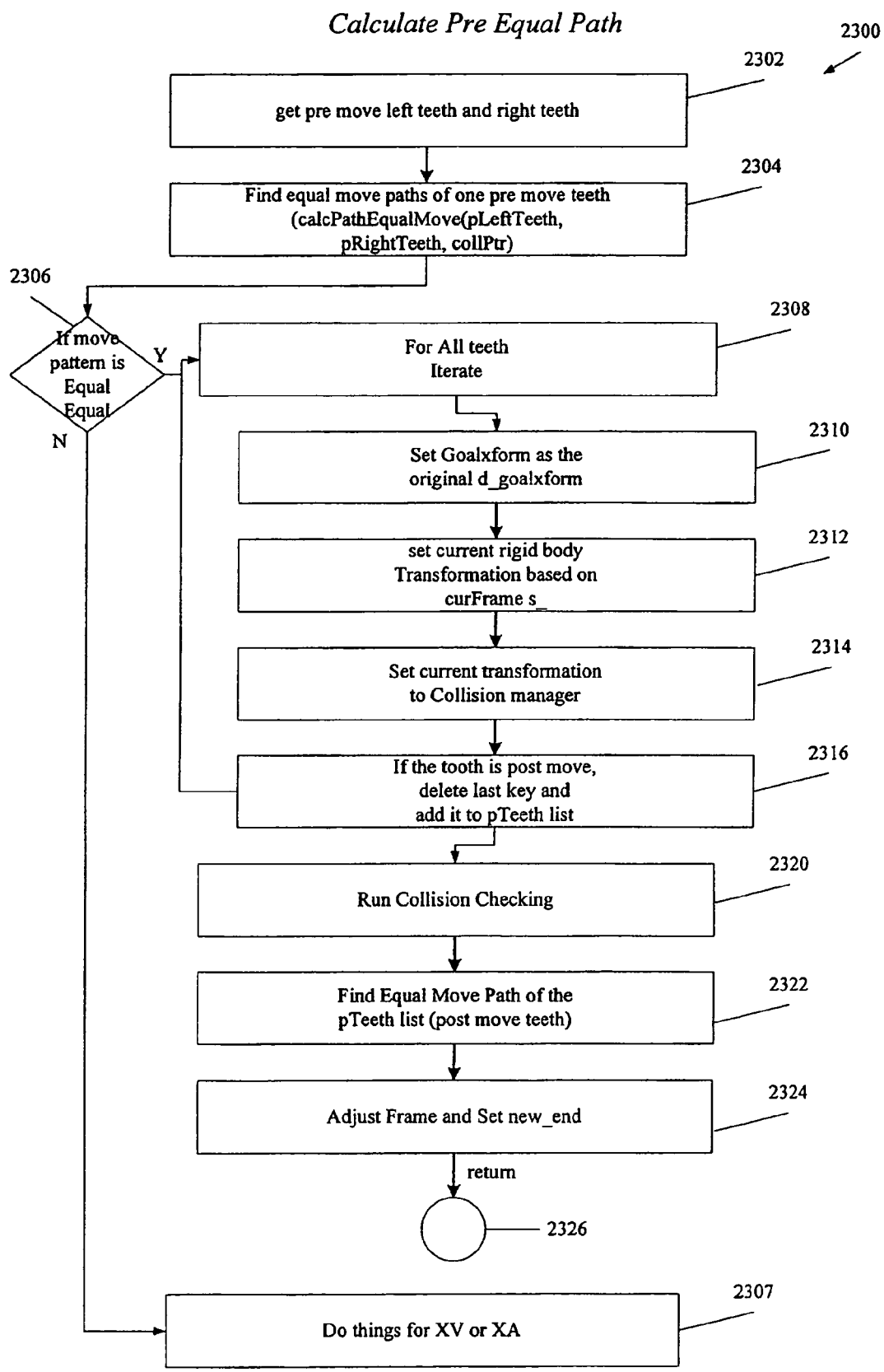
FIG. 19 shows an exemplary process to determine an equal path.

FIG. 19 illustrates an exemplary PreEqual path calculation process 2300. Some move patterns have two distinct phases. The process 2300 is for the move pattern that has an equal movement in the first phase of the movement. First, the process 2300 obtains a pre-move left teeth and right teeth (step 2302). Next, it runs calculating equal move paths with the pre-move teeth (step 2304). The process 2300 then checks whether the post move pattern is also an equal move (step 2306). If so, for all teeth the process iterates in step 2308-2316. In this loop, the process 2300 first sets the current goal transformation as the original goal transformation (step 2310). Next, it sets the current rigid body transformation based on the current frame (step 2312). The process then sets the current transformation to a collision manager (step 2314). Next, it checks whether the tooth should move and if so, it deletes the last key and adds it to the teeth pointer list (step 2316). This iteration sets the teeth at the position from the current transformation, then put the post move teeth into the collision manager.

Upon completing the iteration (step 2308-2316), the process 2300 executes a collision detection operation (step 2320). Next, it executes an equal move path with the post move teeth (step 2322). Finally, the process 2300 runs adjust-frame to refine the frames and sets a new end (step 2324) before it exits (step 2326). From step 2306, if the move pattern is not equal to Equal path, the process performs operations for XV or XA pattern (step 2307).

In summary, the process 2300 calculates a tooth path that has an equal movement pattern in pre-move phase. It runs the calculate equal move for the pre-move teeth, and then if the move pattern is equal-equal, runs another calculate equal move for the post move teeth.

Referring now to FIG. 20A, a process 2400 for calculating a V shaped movement is shown. First, a frame variable is set as the current frame and the teeth list is sorted by its weight (step 2402). Next, for all teeth in the sorted teeth list, the process 2400 performs the following steps. The iteration starts from the leftmost and the rightmost teeth (step 2404). First, the process 2400 operates on a left tooth (step 2406). For the current tooth, the process sets the key frame as the initial transform at current frame and at middle transformation at the frame+1 (step 2408). The middle transformation is interpolated half way from the initial transformation to the goal transformation. Then, the process 2400 sets the key frame to goal transformation at frame+2 and sets the current transformation as the goal transformation. In this manner, each tooth is sequentially moved in three frames. For example, if the current tooth is the left boundary tooth (left canine tooth), the process skips the frame+2, and sets the middle transformation as the current transformation (step 2410). The process 2400 then sets the tooth in the collision manager (step 2412). This loop sets the three-frame move to the tooth, the initial transformation, middle transformation, and the goal transformation except for the boundary tooth. The iteration progresses toward the front teeth in each frame (step 2414).

The same operation is applied to the right teeth (steps 2416 to 2420). Starting from the rightmost tooth, the process sets the three-frame movement for each tooth until it reach the right boundary tooth (right canine). Then, it moves the boundary tooth only to the half way. Both left and right teeth are incrementally processed toward front until both of the boundary teeth are reached (step 2422).

After both the left and right teeth have been processed, the process 2400 further checks whether the frontal space needs to be closed and if so, it executes a closed frontal space function (step 2424).

Figure 20B:
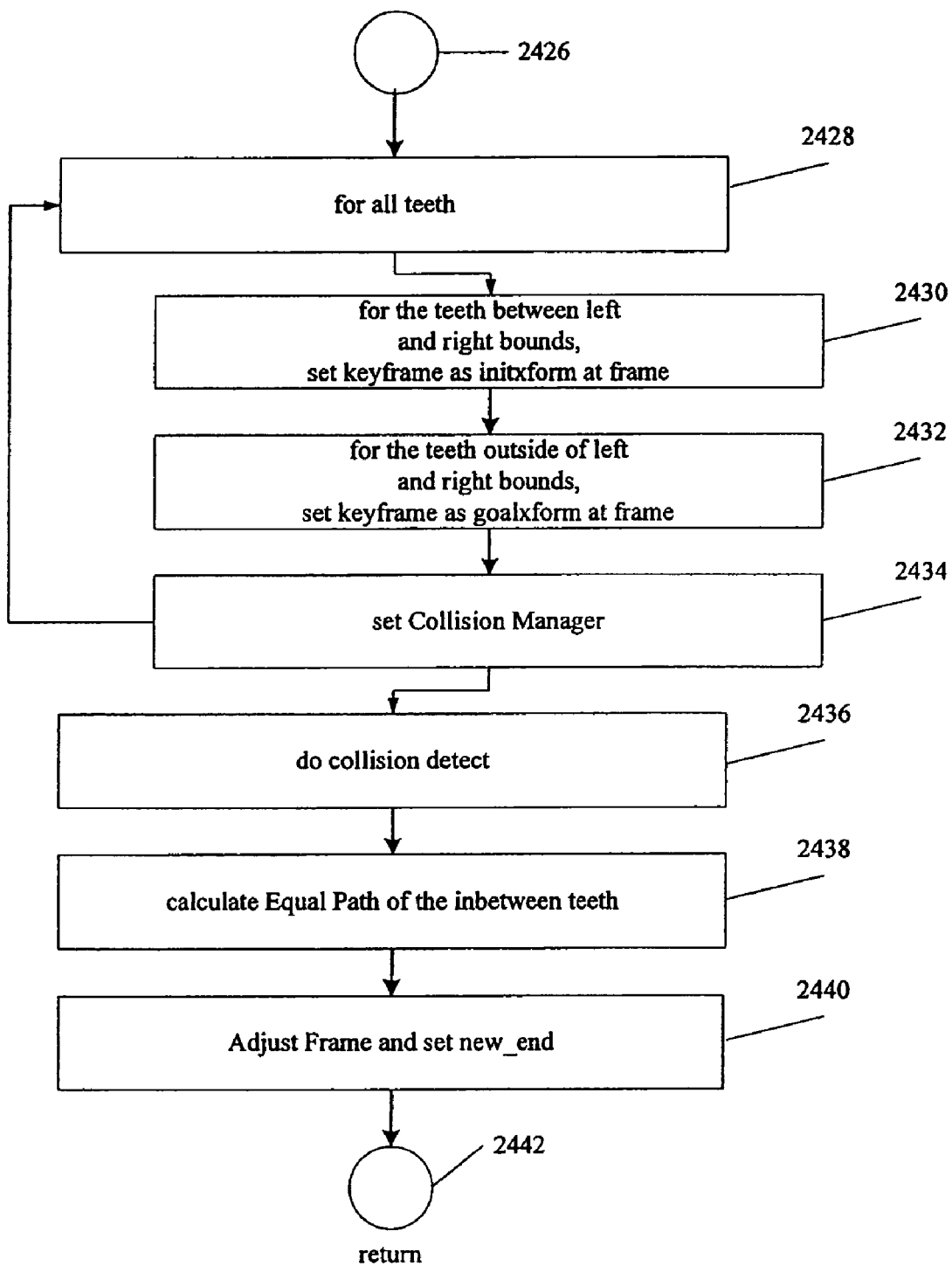

FIG. 20B is a continuation of FIG. 20A through a connector 2426. The process of FIG. 20B continues with another iteration in steps 2428-2434. For all teeth, the process 2400 sets the key frame as the initial transformation at the current frame for anterior teeth, or teeth between the left and the right boundaries (step 2430). For the posterior teeth, or teeth set outside of left and right boundaries, the key frame is set as the goal transform at the current frame (step 2432). All teeth are set to the collision manager to do the collision detection (step 2434).

Upon processing all teeth after step 2434, the process 2400 triggers a collision detection operation (step 2436). Next, it calculates an equal teeth for the anterior teeth (step 2438). Finally, the process 2400 adjusts the frame to refine the frames and sets a new end frame (step 2440) before exiting.

In summary, the V-shape move path is calculated in the opposite direction of the A shape move. It starts from leftmost and rightmost teeth, and sequentially the next ones move until the boundary teeth move. The difference from A-shape move is that the remaining anterior teeth go through an equal move calculation. Thus, V shape move is also a two-phase movement.

The system may also incorporate and the user may at any point use a "movie" feature to show an animation of the movement from initial to target states. This is helpful for visualizing overall component movement throughout the treatment process.

As described above, one suitable user interface for component identification is a three dimensional interactive graphical user interface (GUI). A three-dimensional GUI is also advantageous for component manipulation. Such an interface provides the treating professional or user with instant and visual interaction with the digital model components. The three-dimensional GUI provides advantages over interfaces that permit only simple low-level commands for directing the computer to manipulate a particular segment. In other words, a GUI adapted for manipulation is better in many ways than an interface that accepts directives, for example, only of the sort: "translate this component by 0.1 mm to the right." Such low-level commands are useful for fine-tuning, but, if they were the sole interface, the processes of component manipulation would become a tiresome and time-consuming interaction.

Before or during the manipulation process, one or more tooth components may be augmented with template models of tooth roots. Manipulation of a tooth model augmented with a root template is useful, for example, in situations where impacting of teeth below the gumline is a concern. These template models could, for example, comprise a digitized representation of the patient's teeth x-rays.

The software also allows for adding annotations to the data sets which can comprise text and/or the sequence number of the apparatus. The annotation is added as recessed text (i.e., it is 3-D geometry), so that it will appear on the printed positive model. If the annotation can be placed on a part of the mouth that will be covered by a repositioning appliance, but is unimportant for the tooth motion, the annotation may appear on the delivered repositioning appliance(s).

The above-described component identification and component manipulation software is designed to operate at a sophistication commensurate with the operator's training level. For example, the component manipulation software can assist a computer operator, lacking orthodontic training, by providing feedback regarding permissible and forbidden manipulations of the teeth. On the other hand, an orthodontist, having greater skill in intraoral physiology and teeth-moving dynamics, can simply use the component identification and manipulation software as a tool and disable or otherwise ignore the advice.

Figure 21:
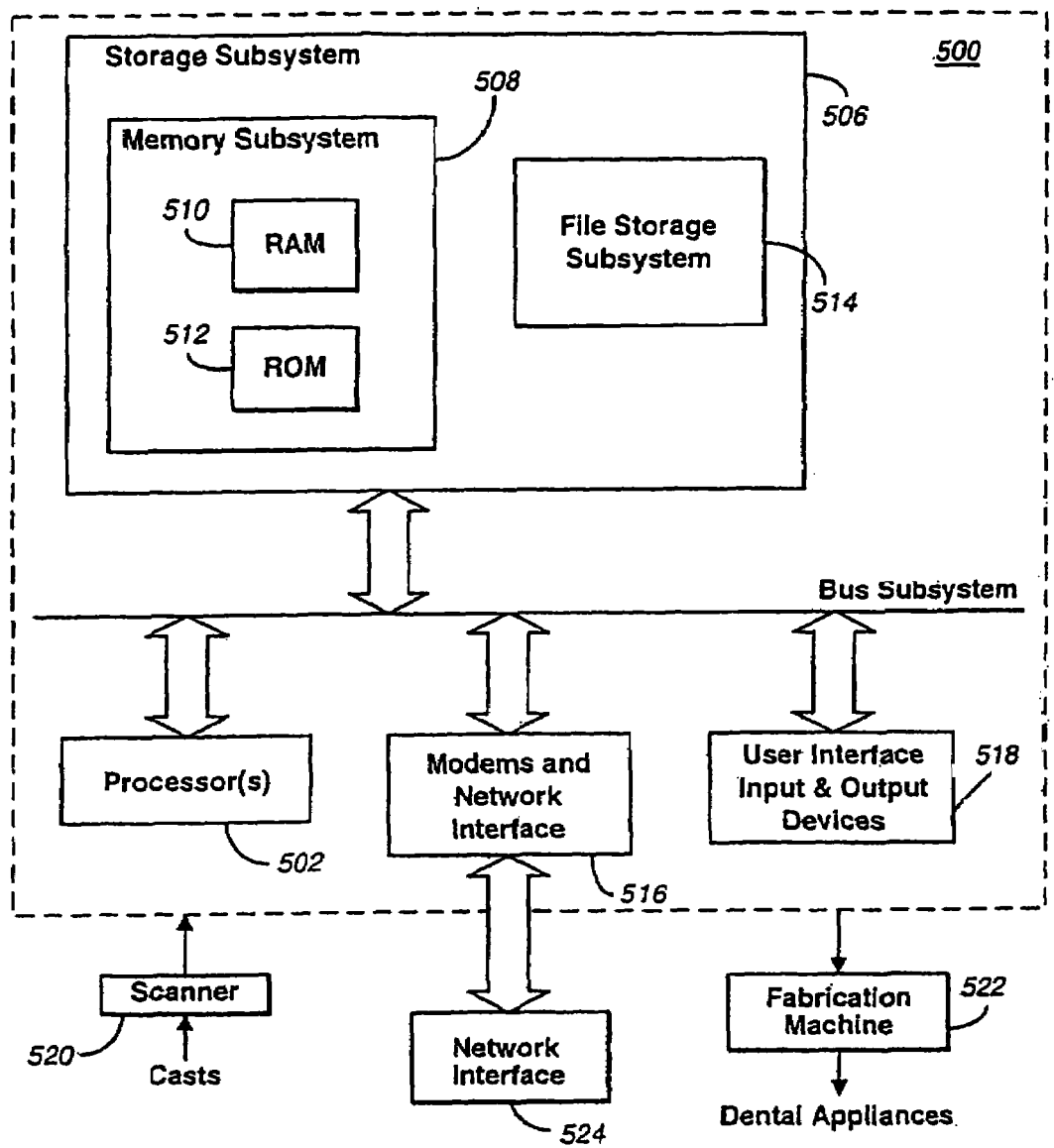
FIG. 21 is a block diagram illustrating a system for generating appliances in accordance with the present invention.

FIG. 21 is a simplified block diagram of a data processing system 500. Data processing system 500 typically includes at least one processor 502 which communicates with a number of peripheral devices over bus subsystem 504. These peripheral devices typically include a storage subsystem 506 (memory subsystem 508 and file storage subsystem 514), a set of user interface input and output devices 518, and an interface to outside networks 516, including the public switched telephone network. This interface is shown schematically as "Modems and Network Interface" block 516, and is coupled to corresponding interface devices in other data processing systems over communication network interface 524. Data processing system 500 may include a terminal or a low end personal computer or a high end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used.

User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output.

Storage subsystem 506 maintains the basic programming and data constructs that provide the functionality of the present invention. The software modules discussed above are typically stored in storage subsystem 506. Storage subsystem 506 typically comprises memory subsystem 508 and file storage subsystem 514.

Memory subsystem 508 typically includes a number of memories including a main random access memory (RAM) 510 for storage of instructions and data during program execution and a read only memory (ROM) 512 in which fixed instructions are stored. In the case of Macintosh-compatible personal computers the ROM would include portions of the operating system; in the case of IBM-compatible personal computers, this would include the BIOS (basic input/output system).

File storage subsystem 514 provides persistent (nonvolatile) storage for program and data files, and typically includes at least one hard disk drive and at least one floppy disk drive (with associated removable media). There may also be other devices such as a CD ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations.

Bus subsystem 504 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 520 is responsible for scanning casts of the patient's teeth obtained either from the patient or from an orthodontist and providing the scanned digital data set information to data processing system 500 for further processing. In a distributed environment, scanner 520 may be located at a remote location and communicate scanned digital data set information to data processing system 500 over network interface 524.

Fabrication machine 522 fabricates dental appliances based on intermediate and final data set information received from data processing system 500. In a distributed environment, fabrication machine 522 may be located at a remote location and receive data set information from data processing system 500 over network interface 524.

Various alternatives, modifications, and equivalents may be used in lieu of the above components. Although the final position of the teeth may be determined using computer-aided techniques, a user may move the teeth into their final positions by independently manipulating one or more teeth while satisfying the constraints of the prescription.

Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices.

Each program can be implemented in a high level procedural or object-oriented programming language to operate in conjunction with a computer system. However, the programs can be implemented in assembly or machine language, if desired. In any case, the language may be a compiled or interpreted language.

Each such computer program can be stored on a storage medium or device (e.g., CD ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

The invention has been described in terms of particular embodiments. Other embodiments are within the scope of the following claims. For example, the three-dimensional scanning techniques described above may be used to analyze material characteristics, such as shrinkage and expansion, of the materials that form the tooth castings and the aligners. Also, the 3D tooth models and the graphical interface described above may be used to assist clinicians that treat patients with conventional braces or other conventional orthodontic appliances, in which case the constraints applied to tooth movement would be modified accordingly. Moreover, the tooth models may be posted on a hypertext transfer protocol (http) web site for limited access by the corresponding patients and treating clinicians.

Further, while the invention has been shown and described with reference to an embodiment thereof, those skilled in the art will understand that the above and other changes in form and detail may be made without departing from the spirit and scope of the following claims.

What is claimed is:

1. A computer-implemented method for preparing digital models of a patient's teeth, said method comprising:
   selecting a tooth treatment pattern from a library of predetermined tooth treatment patterns, the selected pattern comprising an all equal movement pattern, A-shaped movement pattern, V-shaped movement pattern, M-shaped movement pattern, W-shaped movement pattern, symmetric staircase pattern, asymmetric staircase pattern, or equal equal movement pattern;
   calculating tooth movement paths for moving teeth from a first tooth arrangement to a second tooth arrangement and in accordance with the selected treatment pattern; and
   generating computer models representing a series of successive tooth arrangements progressing along the calculated tooth movement paths in accordance with the selected treatment pattern.

2. The method of claim 1, wherein the treatment pattern is selected from one or more clinical treatment prescriptions.

3. The method of claim 2, wherein the one or more clinical treatment-prescriptions includes at least one of the following: space closure, reproximation, dental expansion, flaring, proclination, distalization, and lower incisor extraction.

4. The method of claim 1, wherein determining a tooth path comprises finding a collision free shortest path between an initial position and a final position for one or more teeth.

5. The method of claim 1, wherein calculating tooth movement paths comprises specifying a series of treatment stages for one or more teeth.

6. The method of claim 5, further comprising dividing the path(s) for one or more teeth into the series of stages while keeping the movement of teeth in each stage below a predetermined range.

7. The method of claim 1, further comprising generating an appliance for a treatment stage.

8. The method of claim 7, wherein the appliance is either a removable appliance or a fixed appliance.

9. The method of claim 1, further comprising generating a three-dimensional model for the teeth for a treatment stage.

10. The method of claim 9, further comprising generating dental diagnostic information from the three-dimensional model.

11. The method of claim 9, further comprising generating interproximal reduction information from the 3D model.

12. The method of claim 9, further comprising generating tooth size discrepancy information from the 3D model.

13. The method of claim 9, further comprising generating Bolton information from the 3D model.

14. The method of claim 1, wherein the selected pattern comprises an all equal movement pattern, further comprising subdividing paths while satisfying one or more constraints.

15. The method of claim 14, wherein the constraint comprises minimizing tooth oscillation and tooth movement distance.

16. The method of claim 1, wherein the selected pattern comprises an equal equal pattern, further comprising:
   dividing the teeth into a prestage movement group and a post stage movement group; and
   applying the all equal movement to the prestage movement group and subsequently applying the all equal movement to the prestage movement group.

17. The method of claim 1, wherein the selected pattern is an A-shaped movement pattern, further comprising sequentially moving each tooth from an incisor tooth toward a molar tooth.

18. The method of claim 1, wherein the selected pattern is a V-shaped movement pattern, further comprising sequentially moving each tooth from a molar tooth toward an incisor tooth.

19. A computer-implemented method for preparing digital models of a patient's teeth, said method comprising:
   selecting a tooth treatment pattern from a library of predetermined tooth treatment patterns, the selected pattern comprising an all equal pattern, an A-shaped movement pattern, a V-shaped movement pattern, an M-shaped movement pattern, a W-shaped movement pattern, a symmetric staircase pattern, an asymmetric staircase pattern, or an equal equal movement pattern;
   calculating tooth movement paths for moving teeth based on the selected treatment pattern; and
   generating computer models representing a series of successive tooth arrangements progressing along the calculated tooth movement paths in accordance with the treatment pattern.

* * * * *